US011041168B2

(12) United States Patent
Li et al.

(10) Patent No.: US 11,041,168 B2
(45) Date of Patent: Jun. 22, 2021

(54) APPLICATION OF OSAO GENE FOR IMPROVING RESISTANCE OF RICE AGAINST RICE STRIPE VIRUS, RICE BLACK-STREAKED DWARF VIRUS, OR VIRUS OF SAME FAMILY

(71) Applicant: Peking University, Beijing (CN)

(72) Inventors: Yi Li, Beijing (CN); Xiaofeng Cao, Beijing (CN); Jianguo Wu, Beijing (CN); Zhirui Yang, Beijing (CN); Rongxin Yang, Beijing (CN); Shengze Yao, Beijing (CN); Chunhong Wei, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 16/323,848

(22) PCT Filed: Aug. 11, 2016

(86) PCT No.: PCT/CN2016/094505

§ 371 (c)(1),
(2) Date: Feb. 7, 2019

(87) PCT Pub. No.: WO2018/027713

PCT Pub. Date: Feb. 15, 2018

(65) Prior Publication Data

US 2020/0172921 A1 Jun. 4, 2020

(51) Int. Cl.
*C12N 15/82* (2006.01)

(52) U.S. Cl.
CPC ..... *C12N 15/8283* (2013.01); *C12N 15/8203* (2013.01)

(58) Field of Classification Search
None
See application file for complete search history.

(56) References Cited

U.S. PATENT DOCUMENTS 8,952,218 B2 2/2015 Ayal et al.
2015/0082487 A1* 3/2015 Ayal .................. C12N 15/8262 800/281

FOREIGN PATENT DOCUMENTS

WO WO 2012/028993 A2 3/2012

OTHER PUBLICATIONS

Sequence Accession ATZ16468, Feb. 3, 2011 (sequence alignment is included on the last page of the action) (Year: 2011).*
International Search Report (PCT/ISA/210) dated May 17, 2017, by the State Intellectual Property Office of the P.R. China Patent Office as the International Searching Authority for International Application No. PCT/CN2016/094505 (English Translation).
Written Opinion (PCT/ISA/237) dated May 17, 2017, by the State Intellectual Property Office of the P.R. China Patent Office as the International Searching Authority for International Application No. PCT/CN2016/094505.
Reference XP_015643241.1 for L-ascorbate oxidase isoform X1 [*Oryza sativa* Japonica Group] (Mar. 1, 2016).
Deng Huiying, "The Interaction Between P6 Protein and Other Proteins of Rice Black Streaked Dwarf Virus as well as Proteins of *Oryza Sativa*"; China Academic Literature Database (May 15, 2011), No. 5, ISSN: 1674-0246, pp. 1-54 (See English Abstract).

* cited by examiner

*Primary Examiner* — Elizabeth F McElwain

(57) ABSTRACT

The present application discloses an application of OsAO gene for improving rice resistance to rice stripe disease, rice black-streaked dwarf disease or other rice or corn virus diseases caused by homologous virus of rice black-streaked dwarf virus. The present application also provides an application of OsAO gene, the protein encoded by the gene or a recombinant vector containing the gene in regulating plant resistance to rice stripe disease, rice black-streaked dwarf disease or other rice and corn virus diseases caused by homologous virus of rice black-streaked dwarf virus, said protein has the amino acid sequence as shown in Seq 4. The experiment proved that the plant disease resistance is increased in rice overexpressing OsAO gene, indicating that the OsAO protein encoded by this gene plays an important role in rice resistance to rice stripe disease and rice black-streaked dwarf disease.

4 Claims, 5 Drawing Sheets

Specification includes a Sequence Listing.

APPLICATION OF OSAO GENE FOR IMPROVING RESISTANCE OF RICE AGAINST RICE STRIPE VIRUS, RICE BLACK-STREAKED DWARF VIRUS, OR VIRUS OF SAME FAMILY

RELATED APPLICATION

This application is a U.S. National Phase application of International Patent Application No. PCT/CN2016/094505, filed Aug. 11, 2016. The disclosure of which is herein incorporated by reference in its entirety.

FIELD OF THE INVENTION

The present application belongs to the biotechnological filed, relating to an application of OsAO gene in improving the rice resistance to Rice Stripe Virus and Rice Black Stripe Dwarf Virus.

BACKGROUND OF THE INVENTION

Rice stripe virus disease is a viral disease caused by Rice stripe virus (RSV), which is transmitted by the small brown leafhopper (*Laodelphax striatellus*). It is commonly known as a cancer in rice. Infected plant is often suffered from deathbooting, spike malformation and no seed. During the rice seedling period and the early stage of the disease, yellowish green or yellow-white short spot showed intermittently in the base of heart leaf. Later, the lesion enlarged and merged into yellow-green stripes that parallel to the veins, but it is still green between the stripes. After jointing, yellow-green stripes appeared in the lower part of flag leaf. There is no dead heart in all types of rice, but the infected plants head deformity and barely seed setting.

Rice Stripe Virus is the representative species of Tenuivirus. The virus possesses a unique genome structure and encoding strategy. There are four single-stranded RNAs in the genome. Among them, RNA 2, RNA 3 and RNA 4 adopt an ambisense coding strategy, that is, the sense and antisense strands of RNA have ORF so that they can both encode proteins. RNA2 encodes NS2 and NSvc2 proteins with unknown functions; RNA3 encodes coat protein NCP and RNA silencing suppressor NS3; RNA4 encodes disease specific protein SP and movement protein NSvc4; RNA1 only encodes the RdRp protein.

Rice black-streaked dwarf virus disease is caused by Rice black-streaked dwarf virus (RBSDV), transmitted by the vector small brown rice planthopper (*Laodelphax striatellus*). RBSDV mainly affects the rice in East Asia. The disease can occur in the whole growth cycle of rice, severely affecting the yield of rice. The disease result in rigidity and erectiong of the leaves of infected seedlings, deep green leaves, short and few roots, and growth and development stagnating; at the tillering stage, the susceptible plants will shrink significantly or even die early; at jointing stage, the infected plants will shrink severely, which led to high tiller, inverted eustipes, adventitious roots, and the surface of the stem basement appear longitudinal nodular milky white bulge. At panicle period, the infected plants will be seriously dwarfed, they cannot ear (no heading) or head enclosed neck panicles, their panicle will be smaller and the grain will be less, which will affect rice yield.

The Rice black-streaked dwarf virus, RBSDV, is a member of Fijivirus. The virus can infect maize and wheat and cause virus diseases simultaneously. The virus genome of RBSDV is composed of 10 linear dsRNAs, named S1~S10 from large to small. Among them, S5, S7 and S9 contain two ORFs, while the rest dsRNAs obtain only one ORF. Viral core particles consist of four proteins, P1 (RNA-dependent RNA polymerase), P2 (possibly a core protein), P3 (capping enzyme) and P8 (small core protein), encoded by S, S2, S3 and S8, respectively. P4 and P10 are two outer/coat proteins encoded by S4 and S10. P6 is an RNA silencing suppressor that can deteriorate the disease by interacting with P9-1. P7-2 plays a role in virus infection. Maize rough dwarfvirus (MRDV), a virus that infects maize and cause maize dwarf, belongs to the same family of Reovirus and the same genus of Fijivirus as RBSDV. The MRDV genome is composed of 10 double-stranded RNAs. (Azuhata, F., Uyeda, I., Kimura, I. and Shikata, E. (1993). Close similarity between genome structures of rice black-streaked dwarf and maize rough dwarf viruses. J. Gen. Virol. 74, 1227-1232). The symptom of maize rough dwarf disease is very similar to that of rice black-streaked dwarf disease, which causes large reduction in maize yield in Europe, South America, Southeast Asia and Australia.

Rice Stripe Virus (RSV) and Rice Black Stripe Dwarf Virus (RBSDV) are the major viruses that seriously endanger the rice production in China. Due to the lack of systematic understanding of the interaction mechanism between rice viruses and the hosts, it has been impossible for a long time to design strategies to control the viral diseases thoroughly. Since the mid-1970s, with the rapid development of molecular biology, people have a certain understanding of virus gene structure, viral pathogenicity and plant resistance mechanism, also inspired a series of strategies to control viral diseases by genetic engineering, such as the resistance mediated by coat protein and resistance mediated by post-transcriptional gene silencing. With the accomplish of viral complete genome sequence analysis, the analysis of some important functional genes of viruses, the mature application of efficient rice transgenic technology, the construction of mutant library and the understanding of the interaction mechanism between viruses and hosts, especially the uncover of mechanism of post-transcriptional gene silencing provide innovative possibilities for identifying viral genes pathogenicity and their interaction with host at the level of transgenic molecules as well as for implementing resistance breeding at the level of genetic engineering.

Reactive oxygen species (ROS) are ubiquitous in plants, it is produced in plants under normal growth and environmental stress. ROS produced during plant metabolism includes oxygen anions, hydrogen peroxide and hydroxyl radicals. In plants, ROS is normally produced in chloroplasts, mitochondria, endoplasmic reticulum, plasma membranes and peroxisomes, the reason is that ROS will be generated in the normal redox process, at this time, ROS acts as the second messenger in plants and participates in a series of physiological processes of plant cells, such as stomatal opening and closing, seed germination, cell apoptosis, etc. But when plants are under environmental stress, they will produce a lot of ROS. Excessive ROS will do great harm to plants. On the one hand, ROS will cause the destruction of proteins, lipids and other substances in plants, on the other hand, it will induce cell dissolution or even death. Therefore, the production and removal of ROS in plants is in a dynamic process. Only by removing redundant ROS in plants in time can the normal development of plants be ensured.

Ascorbate oxidase (AO) is an enzyme containing copper. It locates in the cytoplasm and combines with the cell wall. It can oxidize ascorbic acid and couple with other redox reactions. Therefore, AO can participate in the production and removal of ROS through the redox reaction of metal ions. The process that AO participates in the ROS pathway is as follows: AO can oxidize ascorbic acid to monodehydroascorbic acid (MDHA), and ascorbic acid and hydrogen peroxide can produce water under the action of catalase. This process is accompanied by the electron transfer processes of NAD (P) H and NAD (P). Many cycles involve the generation and removal of ROS and these cycles are interrelated. AO plays an important role in this process. In addition to $Cu^{2+}$ can influence ascorbate oxidase, the activity of ascorbate oxidase will also be affected by $Ca^{2+}$, $Al^{3+}$, $K^{+}$, and with the increase of ions concentration, the change trend of the activity of ascorbate oxidase is inhibition—increase—inhibition.

SUMMARY OF THE INVENTION

The object of the invention is to provide an application of OsAO protein and a coding gene thereof for regulating plant resistance to rice stripe disease, rice black-streaked dwarf disease or other rice and corn virus diseases caused by homologous virus of rice black-streaked dwarf virus (i.e., virus from the same family of Rice black-streaked dwarf virus).

The application of the invention includes the following A or B:

A: an application of a protein in a1) or a2):

a1) regulating the resistance of plants to rice stripe disease, rice black-streak dwarf disease or other viral diseases caused by homologous virus of rice black-streaked dwarf virus;

a2) breeding a plant variety that is resistant to rice stripe disease, rice black-streak dwarf disease, or rice or corn viral disease caused by homologous virus of rice black-streaked dwarf virus;

The protein consists of the amino acid sequence shown in SEQ ID NO: 4 in the Sequence Listing or the amino acid sequence which has the same biological activity as SEQ ID NO: 4 and whose sequence identity is at least 95%, preferably above 99% (≥99%) to SEQ ID NO: 4. The biological activity as described therein means to enhance the resistance of plants to rice stripe disease, rice black-streak dwarf disease or rice or corn viral disease caused by homologous virus of rice black-streaked dwarf virus.

B: an application of the gene encoding the protein or a recombinant vector containing the gene in a1) or a2):

a1) regulating the resistance of plants to rice stripe disease, rice black-streak dwarf disease, or rice or corn viral disease caused by homologous virus of rice black-streaked dwarf virus;

a2) breeding a plant variety that is resistant to Rice stripe disease, rice black-streak dwarf disease, or rice or corn viral disease caused by homologous virus of rice black-streaked dwarf virus;

The gene encoding the above-said protein is a DNA molecule according to any one of the following 1) to 4):

1) a DNA molecule shown in SEQ ID NO: 1 in the sequence listing;

2) a DNA molecule shown in SEQ ID NO: 2 in the sequence listing;

3) a DNA molecule which hybridizes to a DNA molecule as defined in 1) or 2) under strict conditions and which encodes said protein;

4) a DNA molecule having 90% or more homology to any of the defined DNA molecules in 1) to 3) and encoding the protein.

As described therein, the protein consisting of the amino acid sequence shown in SEQ ID NO: 4 in the sequence listing is named as OsAO protein (the coding gene is SEQ ID NO: 1, named OsAO genomic sequence, or SEQ ID NO: 2, and named AO Res genomic sequence).

In this invention, regulating the resistance of plants described in the above a1) to rice stripe disease, rice black-streak dwarf disease or other rice or corn viral disease caused by homologous virus of rice black-streaked dwarf virus is embodied in: promoting the expression of the protein or its coding gene, such that the resistance of the plants to rice stripe disease, rice black-streak dwarf disease or other viral diseases caused by homologous virus of rice black-streaked dwarf virus get is improved.

The Method for breeding a plant variety more resistant to rice stripe disease, rice black-streak dwarf disease or other rice and corn viral diseases caused by homologous virus of Rice black-streaked dwarf virus as described in the above a2) specifically include the step of hybridizing the plant having a higher expression level of the protein or its coding gene as a parent.

Another purpose of this invention is to provide a method for breeding transgenic plants with enhanced resistance to rice stripe disease, rice black-streak dwarf disease or other rice or corn viral disease caused by homologous virus of Rice black-streaked dwarfvirus.

The method for breeding transgenic plants with enhanced resistance to rice stripe disease, rice black-streak dwarf disease or other rice or corn viral disease caused by homologous virus of rice black-streaked dwarf virus provided by this invention may specifically include the following steps:

a) Importing a gene encoding a protein into the aimed plants, and obtaining transgenic plants which express the coding gene;

b) Obtaining transgenic plants with enhanced resistance to rice stripe disease, rice black-streak dwarf disease or other rice or corn viral disease caused by homologous virus of rice black-streaked dwarf virus compared to the aimed plants from transgenic plants obtained in step a), wherein the gene encoding a protein is a DNA molecule according to any one of the following 1) to 4):

1) a DNA molecule shown in SEQ ID NO: 1 in the Sequence listing;

2) a DNA molecule shown in SEQ ID NO: 2 in the sequence listing;

3) a DNA molecule which hybridizes to a DNA molecule as defined in 1) or 2) under strict conditions and which encodes said protein;

4) a DNA molecule having 90% or more homology to any of the defined DNA molecules in 1) to 3) and encoding the protein.

The above stringent conditions can use for example the followings: a solution of 6×SSC, 0.5% SDS, hybridized at 65° C., and then washed once with 2×SSC, 0.1% SDS and 1×SSC, 0.1% SDS respectively.

SEQ ID NO: 1 consists of 5472 nucleotides, its positions 1-5472 are the coding sequence of the OsAO gene comprising a 5' UTR, an extron, an intron and a 3'UTR, and its positions 3741-3761 is the miR528 target sequence of the OsAO gene, i.e., the target sequence of the sequence shown in SEQ ID NO: 3, encoding the protein shown in SEQ ID NO: 4 in the sequence listing; SEQ ID NO: 2 consists of 5472 nucleotides, and the coding sequence of the OsAO gene at positions 1-5472 comprises a 5'UTR, an extron, an intron and a 3'UTR, wherein the sequence at positions 3741-3761 is a mutated sequence of the miR528 target sequence of OsAO gene, which is no longer the target sequence of the sequence shown in SEQ ID NO: 3. SEQ ID NO: 3 consists of 21 nucleotides, which is a mature miR528 sequence; SEQ ID NO: 4 consists of 633 amino acids, which is the protein sequence encoded by the OsAO gene; and SEQ ID NO: 5 consists of 15 amino acids, which is the polypeptide site of the protein of SEQ ID NO: 4; SEQ ID NO: 6 consists of 3000 nucleotides and is the endogenous promoter of the OsAO gene.

Those skilled in the art know that the function of the protein encoded by the gene can be affected by point mutation, addition or deletion of one or more bases in the gene sequence. Thus, the invention should be understood to include the above variations in the OsAO gene. The sequence of the OsAO gene is not limited to the SEQ ID NO: 1 in the sequence listing, but also includes a DNA sequence which mutates any codon corresponding to an amino acid residue in the functional region of the protein. It is mainly to mutate functional amino acid residues into alanine which is generally considered to have no special function.

In the method, the gene encoding the protein is introduced into the target plant by a recombinant expression vector containing the gene encoding the protein.

The recombinant expression vector can be constructed by using existing plant expression vectors. The plant expression vector includes a dual *Agrobacterium* vector and a vector which can be used for plant microprojectile bombardment, such as pCAMBIA3301, pCAMBIA2300, pCAMBIA2301, pCAMBIA1300, pCAMBIA 1301, pWM101, pGreen0029, pBI21, pBin19, pCAMBIA301-UbiN, etc. or other derived plants expression vector. The plant expression vector may further comprise a 3'-end untranslated region of a foreign gene, including a polyadenylation signal and any other DNA fragment involved in mRNA processing or gene expression. The polyadenylation signal directs the addition of polyadenylation to the 3'-end of the mRNA precursor. When constructing a recombinant expression vector by using the gene, any enhanced, constitutive, tissue-specific or inducible promoter may be added before the transcription initiation nucleotide, such as Cauliflower mosaic virus (CaMV) 35S promoter, Ubiquitin promoter (pUbi) of Ubiquitin gene, stress-inducible promoter Rd29A, etc., which can be used alone or in combination with other plant promoters; Furthermore, when constructing a recombinant expression vector by using the gene of this invention, an enhancer including a translation enhancer or a transcription enhancer could be used, and these enhancer regions may be an ATG start codon or a contiguous region start codon, etc., but it is necessarily the same reading frame as the coding sequence to ensure correct translation of the entire sequence. The sources of the translational control signals and initiation codons are broad and may be natural or synthetic. The translation initiation region can be from a transcription initiation region or a structural gene. In order to facilitate the identification and screening of transgenic plant cells or plants, the used recombinant expression vector can be processed, for example, adding a gene encoding a color-changing enzyme or luminescent compound that can be expressed in plants, and a resistant antibiotic marker or anti-chemical reagents, etc. Transformed plants can also be screened directly by stress without any selectable marker genes.

In this invention, the promoter that initiates transcription of the coding gene in the recombinant expression vector is specifically an endogenous promoter of the OsAO gene, as shown in SEQ ID NO: 6.

More specifically, the recombinant expression vector is a recombinant plasmid obtained by constructing the coding gene and its promoter onto a pCam1300 expression vector. In the recombinant expression vector, the promoter that initiates transcription of the coding gene is the endogenous promoter of the gene OsAO, as shown in SEQ ID NO: 6.

In the above method, the recombinant expression vector carrying the coding gene is introduced into the target plant specifically by *Agrobacterium*-mediated method, gene gun method, electroporation method, pollen tube introduction method, liposome fusion method and any other method for introducing a plasmid to plants to transform it into plant cells or tissues, and the transformed plant tissues are grown into plants.

In the above application or method, the plant may be a monocot or a dicot.

The monocots are gramineous plants.

In this invention, the plant is rice. Further, varieties of rice preferably are those are sensitive to RSV and RBSDV, such as Zhonghua 11, dongin, Nipponbare (NPB), and Wuyujing 3.

More specifically, in one embodiment of this invention, the background of the rice is Nipponbare, so the background of the transgenic material used is Nipponbare rice, unless otherwise specified.

In the above application or method, the pathogen of the rice stripe disease is specifically Rice stripe virus, and the pathogen of the Rice black-streaked dwarf disease is specifically Rice black-streaked dwarfvirus.

The miR5280E rice and mir528 mutant rice used in this invention are all from Xiaofeng Cao's laboratory, Institute of genetics and development, Chinese academy of sciences, Beiijng, China.

Experiments have shown that the invention finds that OsAO gene is a disease resistance gene that can be induced by RSV and RBSDV. With RSV and RBSDV infection, the accumulations of viral RNA strands in the overexpressed OsAO transgenic rice were significantly lower than that of wild type rice, and the disease symptoms was also mild combined with decreased disease incidence, which have shown that OsAO gene has the ability to improve rice antiviral defense.

The present inventors have found that OsAO is a disease-resistant gene that can be specifically induced by viruses, and in wild type Nipponbare rice infecting by Rice stripe virus (RSV), Rice black streaked dwarfvirus (RBSDV), and Maize rough dwarf virus, the expression of OsAO protein was significantly accumulated. In view of the fact that the above-mentioned rice black-streaked dwarf virus and maize rough dwarf virus belong to the plant Reoviridae, RSV and RBSDV were used in the examples.

When the virus infected rice miR5280E, i.e., rice lines with less AO expression, the accumulation of virions was significantly higher than that of rice wild type, and the disease was more serious, and there was basically no yield. In contrast, when RSV and RBSDV infected the overexpressed OsAO transgenic rice, the accumulation of virions was significantly lower than that of wild-type rice, and the disease was mild, and the incidence decreased, indicating that OsAO gene has the ability to improve rice anti-virus. In view of the fact that rice black streaked dwarf virus can also infect corn, causing corn rough disease, the experimental results show that AO protein or its coding gene can enhance the ability of maize to resist rough corn disease caused by RBSDV, MRDV and the like.

DETAILED DESCRIPTION OF THE PREFERRED EMBODIMENTS

Figure 1:
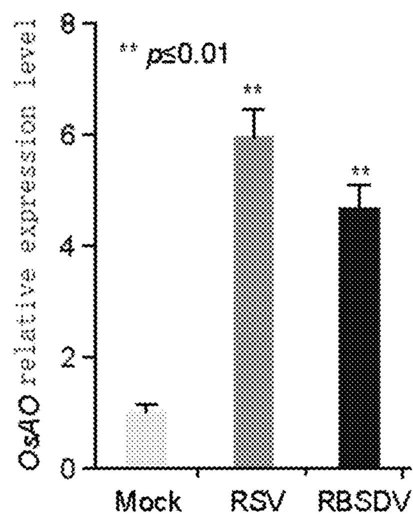
FIG. 1 is detection result of OsAO mRNA accumulations in RSV- and RBSDV-infected WT rice plants in the Nipponbare background. Realtime PCR analysis showed induced OsAO mRNA levels after inoculation with buffer (Mock), RSV and RBSDV. The expression levels were normalized using the signal from OsEF-1α, the relative values were calculated by comparison with the Mock (arbitrarily set to 1.0) wherein OsAO is SEQ ID NO: 1.

The experimental methods used in the following examples are conventional methods unless otherwise specified.

The materials, reagents and the like used in the following examples are commercially available unless otherwise specified.

Rice (*Oryza sativa* L.) cultivar Nipponbare: *Oryza sativa* L. subsp. *japonica* 'Nipponbare', reference: rice cultivar "Nipponbare". Agricultural Science and Technology Newsletter, 1973, 02; available from Peking University.

Rice (*Oryza sativa* L.) cultivar DJ: Dongjin rice (*Oryza sativa* L. subsp. *japonica* 'Dongjin') is a wild-type control of rice T-DNA insertion mutant used in the mutant study, from the mutant rice library in Korea. RISD (http://www.postech.ac.kr/life/pfg/risd/).

Rice (*Oryza sativa* L.) cultivar Wuyujing 3: Susceptible to Rice Stripe Virus (RSV), reference: Wuyujing 3 soil-borne disease occurrence characteristics and control techniques, Jiangsu Agricultural Sciences, 1996 01; available from Peking University.

Rice (*Oryza sativa* L.) cultivar Zhendao 88: Resistant to Rice Stripe Virus (RSV), described in the article "New Rice Cultivar—Zhendao 88, Agricultural Science and Technology Newsletter, 1998 05", available from Peking University.

Rice Stripe Virus (RSV): "Cai Xiaowei, Zhao Junling, Shao Ying, Gui Qingqing, Liu Fang. A review of the research on the transmission of rice stripe virus by *Laodelphax striatellus*. China Plant Protection Guide, 2011 09", available from Peking University.

pAO:AO and pAO:AO-Res transgenic rice were derived from Nipponbare background, recorded in Dr. Yang Rongxin's thesis Functional Research of Rice miRNA528, 2012 10. Dr. Yang was from Cao Xiaofeng's research group, in the Institute of Genetics and Developmental Biology (IGDB) of the Chinese Academy of Sciences (CAS); available from Peking University.

Rice Black-Streaked Dwarf Virus (RBSDV): Chen Shengxiang, Zhang Qiaoyan. Research progress on rice black-streaked dwarf disease and maize rough disease in China. Journal of Plant Protection, Vol. 32, No. 1, 2005; available from Peking University.

*Agrobacterium* EHA105: "Zhu et al., 2005. The Rice Dwarf Virus P2 Protein interacts with ent-Kaurene Oxidases in vivo, leading to reduced biosynthesis of Gibberellins and rice dwarf symptoms. Plant Physiology. 139: 1935-1945"; available from Peking University.

pCam1300 vector: "Jianguo Wu & Zhirui Yang et al., 2015. Viral-inducible Argonaute 18 confers broad-spectrum virus resistance in rice by sequestering a host microRNA. Elife. 2015 Feb. 17; 4"; available from Peking University.

Example 1. Infection of Rice Stripe Virus and Rice Black Streaked Dwarf Virus can Increase the Expression Level of OsAO mRNA The OsAO gene in this example was from rice (*Oryza sativa* L.). The genomic coding sequence of the OsAO gene is composed of 5472 nucleotides, as shown in SEQ ID NO: 1 in the sequence list. The protein encoded by SEQ ID NO: 1 consists of 633 amino acid residues, as shown in SEQ ID NO: 3. The coding sequence of the OsAO gene of the pAO:AO-Res transgenic line is shown in SEQ ID NO: 2, and the encoded protein sequence is shown in SEQ ID NO: 4.

I. OsAO Gene Accumulates after RSV Infection at mRNA Level 0.5 g of leaves per sample from rice Nipponbare infected by RSV or RBSDV and rice not infected by virus (as control) is cut for testing and ground in liquid nitrogen, and total RNA is extracted according to Invitrogen's TRIzol Reagent instruction (Invitrogen Trizol Reagent, cat No. 15596-018). The total RNA concentration is measured, and then the rice genomic DNA in 10 μg of total RNA is digested according to the instructions of RQ1 Dnase (Promega, Cat. No. M610A). Digestion reaction system comprises: 10 μg of total RNA, 10 μl of 10×Dnase buffer, 10 μl of DNase, add DEPC water to 100 μl in total. The entire digestion reaction system is incubated at 37° C. for 35 min, 4 μl of RQ1 DNase stopping solution is added to the system to terminate the reaction, and incubated at 65° C. for 10 min to inactivate DNase.

After digesting the genomic DNA, total RNA is extracted by chloroform, and the total RNA concentration is measured. Then 2 μg of RNA is reverse-transcribed with Invitrogen SuperScript II reverse transcriptase, the primer used is Oligod (T) primer of 16-nucleotide. For detailed protocol, please refer to invitrogen M-MLV Reverse Transcriptase (Cat. No. 28025-021). Using the rice cDNA obtained by reverse transcription as template, the transcriptional level of OsAO gene is detected by real-time quantitative fluorescent PCR according to TOYOBO SYBR® Green Realtime PCR Master Mix (Cat. No. QPK-201), the primers are:

```
AO-qRT-F:
                                   (SEQ ID NO: 7)
5'-CGAGAACGTGGAGACCTGCGTCGA-3';

AO-qRT-R:
                                   (SEQ ID NO: 8)
5'-CCACCACCGTCATCTTGTGCCCTTG-3'.
```

The internal control gene is rice EF, and the primers are:

```
OsEF-la-F:
                                   (SEQ ID NO: 9)
5'-GCACGCTCTTCTTGCTTTCACTCT-3';

OsEF-la-R:
                                  (SEQ ID NO: 10)
5'-AAAGGTCACCACCATACCAGGCTT-3'.
```

For the data processing method, refer to Bio-RAD CFX96 real-time quantitative fluorescence PCR instrument together with software CFX Manager™ Software (Version 2.1).

The results are as shown in FIG. 1. The OsAO gene is significantly enriched after RSV and RBSDV infection in rice at the mRNA level, indicating that the infection of RSV and RBSDV can increase the expression of OsAO gene in rice, such that the transcription level of this gene is increased.

II. OsAO Protein Accumulates in Rice Infected by RSV and RBSDV

The leaves of Nipponbare infected by rice stripe virus (RSV) and rice black streaked dwarf virus (RBSDV) and control (not infected by virus) are used as experimental materials. Total protein is extracted by 2×SDS protein loading buffer, and the accumulation of OsAO protein in different samples is detected by Western blot. The details are as follows:

(1) SDS-PAGE Electrophoresis Procedure and Precautions are According to "SDS-PAGE Gel Electrophoresis of Proteins".

After the electrophoresis, the gel is taken out and the glass plate is removed. The gel is cropped to target size and put in transfer buffer. A piece of ECL membrane slightly larger than the gel and two pieces of extra-thick filter paper are cut, and soaked in transfer buffer.

The transfer sandwich is assembled on the semi-dry transfer cassette base by placing one piece of wet extra-thick filter paper on the bottom, then the ECL membrane, the protein gel, and finally, another piece of the wet filter paper on top. Be careful to remove the any air bubbles with a glass rod during the placement process. The cassette lid is placed and locked. The transfer process is carried out under a constant voltage of 15V for 90 minutes (the transfer time is determined according to the protein size).

1) After transfer process, the membrane is blocked in blocking buffer (5% milk formulated with TBST), and incubated for 1 hour at room temperature or overnight at 4° C.

2) After blocking, the membrane is incubated with a solution of primary antibody (or directly using the recovered primary antibody) diluted in fresh blocking buffer (5% milk formulated with TBST) under gentle agitation for typically 2 hours at room temperature, or overnight at 4° C.

3) Following incubation, the membrane is washed for 3-4 times with TBST wash buffer to remove unbound primary antibody, 5 min for each time, and the primary antibody is recovered.

4) After rinsing, the membrane is incubated with a solution of corresponding fresh secondary antibody diluted in blocking buffer for one hour at room temperature.

5) The membrane is washed for 3-4 times with TBST wash buffer, 5 min for each time.

6) The substrate kit (Immobilon™ Western: MILLIPORE, Shanghai Trading Co., Ltd., Cat. No. 1305701) corresponding to the enzyme coupled to the secondary antibody is developed and added to the membrane. After 1 minute of incubation reaction, the excess liquid on the membrane is exhausted. Try not to let the film dry, wrap it in plastic wrap as soon as possible, put it in a dark clip, expose it with X-ray film and develop, and finally scan the good film and save it.

(2) Reagents Required for the Experiment:

1) 10 mL of 2×SDS protein loading buffer: 2 mL glycerol, 0.202 g bromophenol blue, 1 mL of 1 M Tris-HCl (pH 6.8), 0.14 mL β-mercaptoethanol, 4 mL 10% SDS, add $H_2O$ to 10 mL, stored at −20° C.

2) 1 L of Transfer buffer: 2.9 g of 39 mM glycine, 5.8 g Tris, 0.37 g of SDS, 200 mL methanol.

3) 100 mL of Alkaline phosphatase buffer: 100 mM NaCl, 5 mM $MgCl_2$, 100 mM Tris-HCl, pH 9.5.

4) 1 L Tris-Buffered Saline with 0.1% Tween 20 (TBST): 2.42 g Tris, 8 g NaCl, 1 mL Tween 20, 900 mL water, pH is adjusted to a constant volume of 1 L, pH 7.6.

5) 100 mL Blocking buffer: 5 g non-fat dry milk in 100 mL TBST.

Actin protein is used as the internal control. The primary antibody is Actin monoclonal antibody (from mouse, Sigma, Cat. No. T6793). The secondary antibody is anti-mouse (Promega, Cat. No.: 0000089661).

Figure 2:
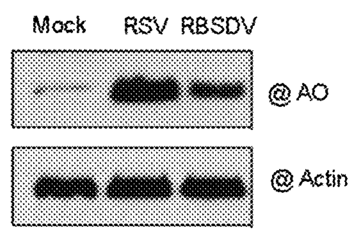
FIG. 2 is detection result of OsAO protein (SEQ ID NO: 4) accumulations in mock-, RSV- and RBSDV-infected WT rice plants. Mock represents wild type rice Nipponbare not infected by RSV or RBSDV; RSV represents wild type rice Nipponbare infected by RSV; RBSDV represents wild type rice Nipponbare infected by RBSDV. Actin was detected and used as a control.

The results are as shown in FIG. 2. The expression level of OsAO protein is low in the control rice (wild type Nipponbare not infected by RSV nor RBSDV), but is relatively high in wild type NPB infected by RSV or RBSDV. This result indicates that the infection of RSV and RBSDV can also increase the expression of OsAO protein in translational level.

III. AO Enzyme Activity Increases after Infection by Rice Stripe Virus and Rice Black streaked dwarf virus.

The leaves of wild type rice (*Oryza sativa* L.) cultivar Nipponbare infected by rice stripe virus (RSV) or rice black streaked dwarf virus (RBSDV) and control rice (NPB not infected by rice stripe virus nor rice black stripe) are sampled to detect the activity of AO as follows:

1) Preparation of Ascorbate Oxidase Extraction:

100 mg of plant stem and leaf tissue is ground to powder in liquid nitrogen, 1 mL of 10 mM PBS (pH 6.5) is added to dissolve and homogenized using vortex. The resulting material is placed on ice for 20 min, shaken every 5 min, and centrifuged at 4° C., 15000 g for 20 min; the supernatant is transferred to a new tube, which is the ascorbate oxidase extraction, and placed on ice and ready for use.

2) Detection of Ascorbate Oxidase Activity:

The assay mixture consists of 10 μL of the extraction, 80 μL of 10 mM PBS (pH 5.6) and 10 μL of 2 mM L-AsA (L-ascorbic acid). The absorbance of A265 is measured with a Thermo full-wavelength microplate reader. Each sample have 3 to 5 replicates, and a mixture without the extraction is used as blank to compare the decrease in the absorbance of A265. The extinction coefficient (6) is 14.3 $mM^{-1}$ $cm^{-1}$.

Figure 3:
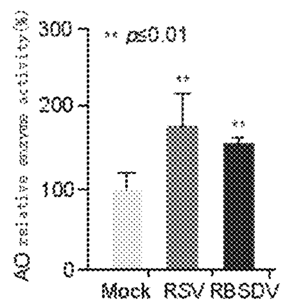
FIG. 3 is detection result of relative enzyme activity of AO after mock, RSV or RBSDV infection. The results were based on the assumption that the relative enzyme activity of the Mock was 100%.

The results are as shown in FIG. 3. The OsAO protein has lower activity in the control rice (Nipponbare not infected by RSV nor RBSDV), but has higher enzymatic activity in NPB (*Oryza sativa* L.) infected by rice stripe virus (RSV) or rice black-streaked dwarf virus. This result indicates that the enzyme activity of OsAO protein can be induced by infection of rice stripe virus (RSV) or Rice black-streaked dwarf virus (RBSDV).

Example 2. Enhanced Rice Antiviral Defense Against Rice Stripe Virus of OsAO Overexpression Transgenic Rice Lines I. The Accumulation of AO in pAO: AO and AO-Res Transgenic Rice is Significantly Higher than that in Wild Type Rice Nipponbare (NPB)

1. The mRNA Levels of AO in pAO: AO and AO-Res Transgenic Rice are Significantly Higher than that in Wild Type.

Some leaves of pAO: AO, AO-Res transgenic rice and wild type rice are ground in liquid nitrogen, total RNA is extracted, and real-time quantitative fluorescent PCR is performed to detect AO mRNA level. The method is carried out by referring to step 1 of example 1.

Primer Sequences are Listed as Follows:

```
AO-qRT-F:
                                    (SEQ ID NO: 11)
5'-CGAGAACGTGGAGACCTGCGTCGA-3';

AO-qRT-R:
                                    (SEQ ID NO: 12)
5'-CCACCACCGTCATCTTGTGCCCTTG-3'.
```

The reference gene is OsEF gene in rice and the primers sequence are:

```
OsEF-1a-F:
                                    (SEQ ID NO: 13)
5'-GCACGCTCTTCTTGCTTTCACTCT-3';

OsEF-1a-R:
                                    (SEQ ID NO: 14)
5'-AAAGGTCACCACCATACCAGGCTT-3'.
```

Figure 4:
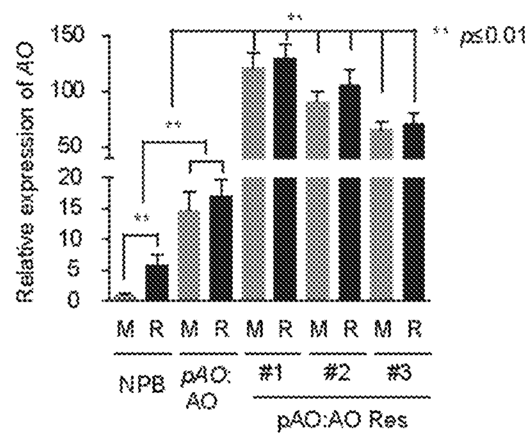
FIG. 4 is detection result of OsAO mRNA expression levels in mock-(M) or RSV-inoculated (R) WT (Nipponbare, NPB) and pAO:AO and pAO:AO-Res transgenic rice lines. In the uninfected rice, the expression levels of OsAO mRNA were significantly increased in pAO:AO and pAO:AO-Res lines relative to NPB. In the RSV-infected rice plants, there was a marked rise in OsAO mRNA expression levels compared with the mock. OsEF-1α was served as a loading control, the expression levels in the Mock plants are set to a value of 1.0 and the expression levels in the other plants are relative to this reference value.

From the results in FIG. 4, it can be seen that compared with the non-transgenic wild type rice (*Oryza sativa* L.) variety Nipponbare, the expression of OsAO gene in pAO: AO and AO-Res transgenic rice plants is higher, especially pAO: AO-Res transgenic line.

2. AO mRNA Levels are Significantly Increased in pAO: AO and AO-Res Transgenic Rice after Virus Infection.

Non-transgenic wild-type rice cultivar Nipponbare, pAO: AO and pAO: AO-Res transgenic rice lines are infected with RSV or non-toxic *Laodelphax striatellus* in the same stage (tillering stage), in which the corresponding rice infected with non-toxic ash fly is used as a control group. The inoculated and control pAO:AO and AO-Res transgenic rice and wild type partial leaves are ground in liquid nitrogen to extract total RNA, and real-time quantitative fluorescent PCR is used to detect AO mRNA level. The method was carried out in accordance with step 1 of Example 1.

The results are shown in FIG. 4. As can be seen from the figure, compared with the uninfected control rice, the mRNA levels of AO in all lines after infection are increased, especially in the pAO:AO and AO-Res transgenic rice.

3. The Relative Enzyme Activity of AO in pAO: AO and AO-Res Transgenic Rice is Significantly Higher than that of Wild Type Rice Nipponbare (NPB).

For the specific operation, refer to step III in example 1.

Figure 5:
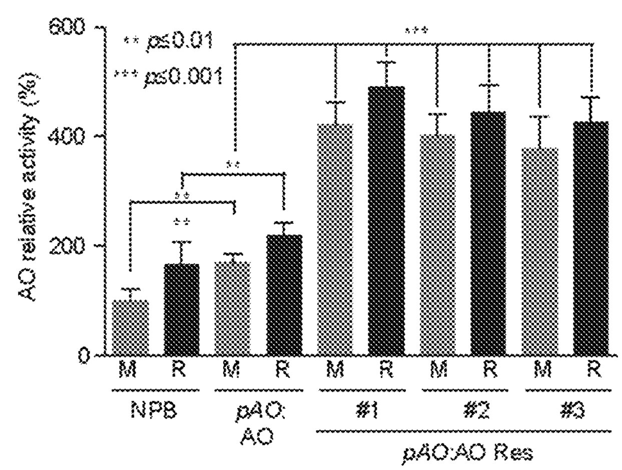
FIG. 5 is detection result of relative enzyme activity of OsAO in mock-(M) or RSV-inoculated (R) WT(NPB) and pAO:AO and pAO:AO-Res transgenic rice lines. The enzyme activity of OsAO significantly increased in pAO:AO and pAO:AO-Res lines than NPB in the mock plants. And the enzyme activity of OsAO was dramatically higher after RSV infection.
Figure 6:
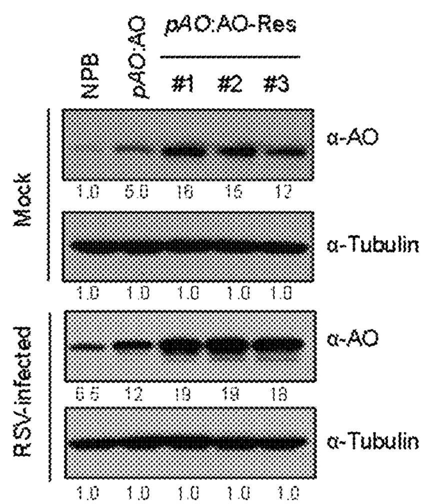
FIG. 6 is detection result of OsAO protein (SEQ ID NO: 4) levels in WT(NPB) and pAO: AO and pAO:AO-Res transgenic rice lines with (R) or without (M) RSV infection. The OsAO expression levels was greatly enhanced in pAO:AO and pAO:AO-Res lines when compared with NPB. In contrast with the uninfected, the OsAO expression levels in the RSV-inoculated plants increased significantly. α-Tubulin was probed and served as a loading control.

The results are shown in FIG. 5. As can be seen from the figure, compared with the non-transgenic wild type rice (*Oryza sativa* L.) variety Nipponbare, the relative enzyme activity of OsAO in pAO:AO and AO-Res transgenic rice plants is significantly increased, especially in pAO: AO-Res line. At the same time, the enzyme activity of OsAO is also increased significantly after virus infection.

4. The Accumulation of OsAO Protein in pAO: AO and AO-Res Transgenic Rice is Significantly Higher than Wild Type Rice Nipponbare (NPB).

For the specific operation, refer to step III in example 1.

The results are shown in FIG. 5. As can be seen from the figure, compared with the non-transgenic wild type rice (*Oryza sativa* L.) variety Nipponbare, the accumulation of OsAO protein in pAO:AO and AO-Res transgenic rice is increased significantly, especially in pAO: AO-Res line. At the same time, the protein accumulation of AO was also significantly up-regulated after virus infection.

II. pAO: AO and AO-Res Transgenic Rice has Increased Resistance to RSV.

1. After RSV Infects pAO: AO and AO-Res Transgenic Rice, the Disease is Relieved, and the Incidence is Significantly Reduced.

Non-transgenic wild-type rice cultivar Nipponbare, pAO: AO and pAO: AO-Res transgenic rice lines are infected with *Laodelphax striatellus* carrying RSV in the same stage (tillering stage), in which the corresponding rice infected with non-toxic ash fly is used as a control group.

After 2 weeks, the incidence of rice is detected (the identification of rice incidence refers to the literature "Chapter 1.1 of the Identification and Control of Major Virus Diseases in Rice and Wheat"), and the incidence rates of the experimental group and the control group are statistically calculated. Simultaneously, the difference of the phenotypes after the onset of rice among different experimental groups is observed.

Figure 7:
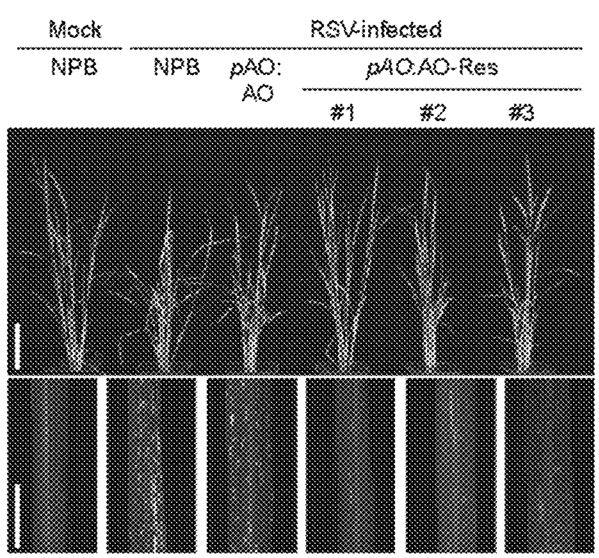
FIG. 7 shows symptoms of mock- or RSV-inoculated WT(NPB) and transgenic plants expressing pAO:AO or pAO:AO-Res in the NPB background in example 3. The symptom of pAO:AO and pAO:AO-Res lines was apparently attenuated compared to NPB after RSV infection.

In the experimental group, the statistical results of the incidence of each rice line are shown in Table 1. It can be seen from the table that the incidence of pAO:AO and pAO:AO-Res transgenic rice infected by RSV was significantly lower than that of wild-type rice cultivar Nipponbare. Further, the symptoms of each rice line inoculated with RSV is shown in FIG. 7. After RSV infects pAO:AO and pAO: AO-Res transgenic rice lines, the disease is lighter than wild type rice, and the green streak is reduced. The incidence of the leaves is also reduced.

TABLE 1

Statistics of incidence of OsAO and OsAO-Res overexpressing rice after RSV infection.

| Rice line | N[a] | D[b] | P[c] |
|---|---|---|---|
| NPB | 73 | 41 | 56.16% |
| pAO:AO | 75 | 29 | 38.67% |
| pAO:AO-Res #1 | 73 | 24 | 32.87% |
| pAO:AO-Res #2 | 74 | 27 | 36.47% |
| pAO:AO-Res #3 | 75 | 29 | 38.66% |

Note:
[a]the total number of rice plants observed;
[b]the number of rice plants with disease phenotype after two weeks of infection;
[c]the proportion of diseased rice relative to all infected rice;
[d]control without the preference of insect mediators to rice lines.

The above experimental results show that the overexpression of OsAO gene in pAO:AO and AO-Res transgenic rice lines enhances the disease resistance of plants, making rice less susceptible to RSV infection.

2. Northern Blot Analysis about Accumulation of RNA Strands of RSV Genome in Diseased Rice The wild-type rice variety Nipponbare, diseased pAO:AO and pAO:AO-Res transgenic rice, undiseased wild-type rice variety Nipponbare, undiseased pAO:AO and pAO:AO-Res transgenic rice obtained in step 1 are used as an experimental material. 2 g of each rice leaf is taken and ground into powder in liquid nitrogen, and total RNA is extracted according to the Invitrogen TRIzol Reagent specification (Invitrogen Trizol Reagent, cat No. 15596-018), and the resulting samples are ready for use after measuring the concentration.

A. 120 mL of 1.2% agarose formaldehyde denatured gel is prepared in a ventilated cabinet: 1.44 g agarose is added to 87.6 mL DEPC water, heated in a microwave to melt the agarose, then cooled to a temperature of about 60° C. Thereto 12 ml 10×mops stock solution and 20.4 mL of formaldehyde is added. After shaking and mixing well, the resulting mixture is quickly poured into the gel groove and insert the comb.

B. RNA loading buffer is added to 10-20 μg RNA sample, heated at 100° C. for 10 minutes, and then placed on ice for 2-3 min, and centrifuged for 1-2 min before loading.

C. the denatured sample is added by pipette to the cooled agarose formaldehyde denaturing gel. The electrophoresis solution is 1×mops solution, and at voltage of 100V, electrophoresis is carried out for 3-4 hours. The gel is cut and placed in a 20×SSC solution for 10-20 min.

D. After electrophoresis is completed, two methods, i.e., vacuum transfer and capillary transfer are used for transmembrane. The basic method of capillary transfer comprises: 20×SSC solutions is poured into the culture dish, and 2-3 layers of filter paper are placed on the glass plate to form a paper bridge. The gel is put on the paper bridge, the PDVF film is placed on the top of the gel, and thereto 3 layers of filter paper and 10-25 cm thick of absorbent paper are put. A weight is pressed thereon again and transferring (transmembrane) is conducted for 24-36 hours. The principle of vacuum transfer is the same as that of capillary transfer, using a vacuum pump to speed up the transfer of the solution.

E. UV crosslinking: the film is crosslinked at the energy of 1800. The film can then be baked at 80° C. for 30 min. The treated film can be stained with methylene blue, and tested about the presence or absence of degradation of the RNA in the previous step and whether the amount of sample loading is consistent. The band of the dyed rRNA can be used as a control.

F. The film is placed in a hybridization flask containing a pre-mixed liquid (Sigma, serial number SLBG7228V), and pre-mixed at 65° C. for 1-2 hours.

G. The labeled probe (primer sequences for amplifying the four RNA strand probes is shown below) was denatured at 100° C. for 10 min and then placed on ice for 3 min to cool. This is added to the pre-mixed solution and hybridized overnight (over 24 hours) at 65° C. Labeled Probes Random Primer Reaction System refers to the method provided by TAKARA Probe Labeling Kit (Cat. No. D6045):

| | |
|---|---|
| $ddH_2O$ added to 50 μl volume | 29 μl |
| Labeling 5× buffer | 10 μl |
| unlabeled dNTPs mixture | 2 μl |
| Denatured RNA template (30-50 ng) | 1 μl |
| BSA | 2 μl |
| α-32P dCTP (50 μCi, 3000 Ci/mmol) | 5 μl |
| DNA Polymerase I Klenow Large Fragment (5 U) | 1 μl |

The primers used to amplify the four RNA strand probes are shown below (5'-3')

```
RSV-RNA1-F:
                                    (SEQ ID NO: 15)
5'-GCACCCAATAGGTATCTCCTTGAT-3';

RSV-RNA1-R:
                                    (SEQ ID NO: 16)
5'-CAAATGACCCTACTAGATGGACGA-3'.

RSV-RNA2-F:
                                    (SEQ ID NO: 17)
5'-CAACCACCCTTATCACAAACTTCA-3';

RSV-RNA2-R:
                                    (SEQ ID NO: 18)
5'-CACCAATACCTTTCCCTGACACCC-3'.

RSV-RNA3-F:
                                    (SEQ ID NO: 19)
5'-TATATGGGCACCAACAAGCCAGCC-3';

RSV-RNA3-R:
```

-continued

```
                                  (SEQ ID NO: 20)
5'-TATGACTTAGGGAGTGAGTTGTGCAGT-3'.

RSV-RNA4-F:
                                  (SEQ ID NO: 21)
5'-GCTTCACCACACCGAACTCCTTCT-3';

RSV-RNA4-R:
                                  (SEQ ID NO: 22)
5'-GTTACGATTGACCAAGCTGCCACA-3'.
```

H. After the hybridization is completed, the film is washed twice with a 2× is washing solution (2×SSC, SDS is added to a final concentration of 1 g/L) at 65° C. for 20 minutes each time. Then, a 0.1× washing solution (0.1×SSC, SDS is added to a final concentration of 1 g/L), and the film is washed once at 65° C. for about 20 minutes.

I. The film is air-dried and wrapped with plastic wrap to measure the radiation intensity. Tableting (X-ray film or phosphor screen) is carried out, and the length of the tableting time is determined according to the radiation intensity.

rRNA is used as a control in the experiment.

Figure 8:
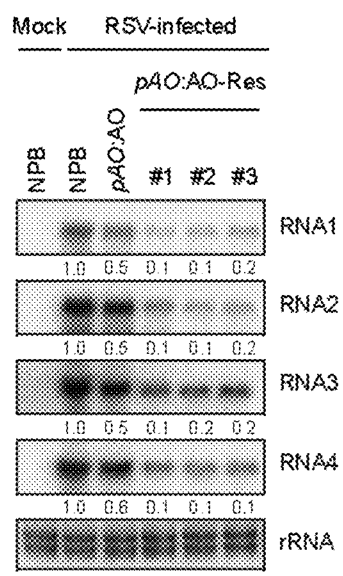
FIG. 8 shows the accumulation amount of RSV virus in mock- or RSV-inoculated WT(NPB) and transgenic plants expressing pAO:AO or pAO:AO-Res in the NPB background in example 3. Compared with NPB, the accumulation of four RNA strands of the RSV virus in pAO:AO and pAO:AO-Res lines reduced after RSV infection.

J. The experimental results are shown in FIG. 8, the enrichment of the four RNA strands of the RSV genome in the pAO:AO and pAO:AO-Res transgenic rice lines is lower than that of the wild type rice Nipponbare, which further indicates that the amount of replication of RSV in pAO:AO and pAO:AO-Res transgenic rice lines is relatively small. This is consistent with the results measured in step 1: the pAO:AO and pAO:AO-Res transgenic rice lines are more resistant to disease than the wild type rice variety Nipponbare.

K. The above results all proved that the OsAO gene is involved in rice defense against rice stripe virus. After overexpressing the gene in rice, the plant is more resistant to disease, the disease is weakened, and the amount of virion replication is reduced.

Example 3: Enhanced Ability of Transgenic Rice Overexpressing OsAO Against Rice Black Streak Dwarf Disease I. pAO: AO-Res Transgenic Lines and Mir528 Mutant Rice have Enhanced Resistance to RBSDV 1. After RBSDV Infects pAO: AO-Res Transgenic Lines and Mir528 Mutant Rice, the Disease is Alleviated and the Incidence is Significantly Reduced.

Non-transgenic wild-type rice cultivar Nipponbare, pAO: AO-Res transgenic rice line, miR5280E rice, and mir528 mutant rice and wild type DJ are infected with *Laodelphax striatellus* carrying RBSDV virus in the same stage (Tiller period). The corresponding rice is infected with non-toxic *Laodelphax striatellus* (gray planthopper) as a control group.

After 2 weeks, the incidence of rice was detected (the identification of rice incidence refers to Chapter 1.3 of the book《Identification and Control of Major Virus Diseases in Rice and Wheat》), and the incidence rates of the experimental group and the control group are statistically analyzed. Simultaneously, the difference of the phenotypes after the onset of rice among different experimental groups is observed.

Figure 9:
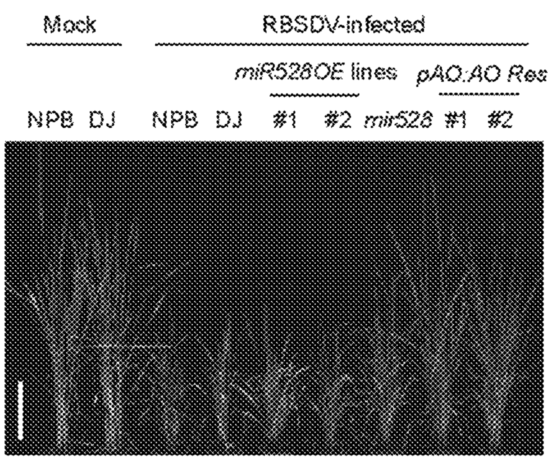
FIG. 9 shows symptoms of mock- or RBSDV-inoculated DJ, NPB, mir528 and transgenic lines expressing pAO:AO-Res(pAO:AO-Res) or overexpressing miRNA528 (miR5280E) in example 3. DJ and NPB are wild type rice, miR5280E is transgenic rice overexpressing miRNA528 in the NPB background, mir528 is the mutant rice of microRNA528 in the DJ background, pAO:AO-Res is the transgenic rice with NPB background.

In the experimental group, the statistical results of the incidence of each rice line are shown in Table 2. It can be seen from the table that the incidence of RBSDV-infected pAO:AO-Res transgenic rice lines and mir528 mutants with higher AO expression is significantly lower than that of RBSDV-infected wild-type rice varieties Nipponbare and DJ. Further, the symptoms of each rice line inoculated with RBSDV virus is shown in FIG. 9. After RBSDV infects the line with higher AO expression, i.e., mir528 mutant and pAO: AO-Res transgenic rice line, the disease is significantly lighter than wild-type rice, especially in pAO: AO-Res transgenic lines, plant dwarfing is weakened or even no dwarfing.

TABLE 2

Statistics of incidence after RBDSV infection of OsAO and OsAO-Res overexpression rice

| Rice line | N[a] | D[b] | P[c] |
|---|---|---|---|
| NPB | 75 | 55 | 73.33% |
| DJ | 73 | 52 | 71.93% |
| miR528OE#1 | 73 | 62 | 84.93% |
| miR528OE#2 | 73 | 60 | 82.19% |
| mir528 | 75 | 39 | 52% |
| pAO:AO-Res#1 | 75 | 31 | 41.33% |
| pAO:AO-Res#2 | 75 | 31 | 41.33% |

2. After RBSDV Infects pAO: AO-Res Transgenic Lines and Mir528 Mutant Rice, the Virus Accumulation is Less.

The diseased wild type rice varieties Nipponbare and DJ, diseased pAO: AO-Res transgenic rice, diseased mir528 mutant and the miR5280E line and undiseased lines obtained in the step 1 are used as experimental materials. 2 g of each rice leaf material is ground into powder in liquid nitrogen. Total RNA is extracted according to Invitrogen TRIzol Reagent instructions (Invitrogen Trizol Reagent, cat No. 15596-018) for further detection of RBSDV four genomic RNA strands (S1,S2,S6,S10) by qRT-PCR. The specific experimental steps refer to step I of the example 1.

The primer sequences used in the experiment are as follows (5'-3')

```
RBSDV-S1-F:
                                  (SEQ ID NO: 23)
5'-AACCCAGTCAAGACGCTCA-3';

RBSDV-S1-R:
                                  (SEQ ID NO: 24)
5'-CGACATCAAATGAAGCACCT-3'.

RBSDV-S2-F:
                                  (SEQ ID NO: 25)
5'-TGTGATAACAGAATGACGGC-3';

RBSDV-S2-R:
                                  (SEQ ID NO: 26)
5'-CTTCGGTCGGACAATACAC-3'.

RBSDV-S6-F:
                                  (SEQ ID NO: 27)
5'-TCAGCAGTCTTGGGTTGAT-3';

RBSDV-S6-R:
                                  (SEQ ID NO: 28)
5'-CAGTTTCAGCAGAGTAACGC-3'.

RBSDV-S10-F:
                                  (SEQ ID NO: 29)
5'-ATTGGCGAAGTGTTGAGC-3';

RBSDV-S10-R:
                                  (SEQ ID NO: 30)
5'-CGGGTGCTAAATGAAATGC-3'.
```

Figure 10:
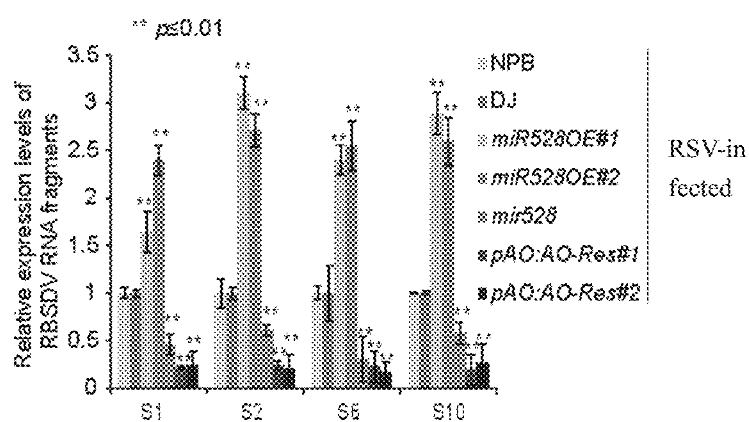
FIG. 10 shows the accumulation amount of RBSDV virus in mock- or RBSDV-inoculated DJ, NPB, mir528, and pAO:AO-Res or miR5280E transgenic lines in example 3. S1, S2, S6, and S10 are four representative viral chains of RBSDV. OsEF-la was probed and served as a loading control, the expression levels of each chain in the RBSDV-infected NPB plants are set to 1.0 and the expression levels in the other plants are relative to this reference value.

The results are shown in FIG. 10. In the pAO:AO-Res transgenic rice and mir528 mutants with relatively high AO expression, the accumulation of viral RNA strands is less than that of the wild type, while the accumulation of the four RNA strands of the virus in the miR5280E rice with relatively low AO expression is higher than that of the wild type, which is consistent with the phenotype observed in FIG. 9.

II. The Accumulation of OsAO and the Enzyme Activity of OsAO Protein in Rice are Up-Regulated after RBSDV Infection.

1. After RBSDV Infects Different Rice Lines, the mRNA Level of OsAO is Up-Regulated.

The diseased wild type rice varieties Nipponbare and DJ, the pathogenic pAO: AO-Res transgenic rice, diseased mir528 mutant and miR5280E line and undiseased lines obtained in step I are used as experimental materials. 2 g of each rice leaf material is taken and ground into powder in liquid nitrogen. Total RNA is extracted according to Invitrogen's TRIzol Reagent instruction (Invitrogen Trizol Reagent, cat No. 15596-018) for further detection of OsAO mRNA accumulation by qRT-PCR. The specific experimental steps refer to step I of Example 1.

Figure 11:
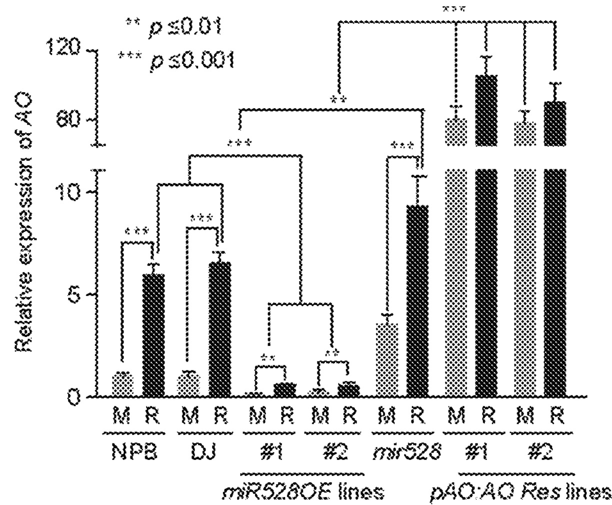
FIG. 11 is detection result of OsAO mRNA expression levels in mock-(M) or RBSDV-inoculated(R) DJ, NPB, mir528, and pAO:AO-Res or miR5280E transgenic lines in example 3, wherein M represents uninfected rice, R represents RBSDV-inoculated rice.

The results are shown in FIG. 11. The mRNA level of OsAO is significantly up-regulated after RBSDV infection, indicating that the expression of OsAO is induced in plants infected with RBSDV.

2. The Relative Enzyme Activity of OsAO is Enhanced after RBSDV Infects Rice of Different Lines.

The diseased wild type rice varieties Nipponbare and DJ, diseased pAO: AO-Res transgenic rice, diseased mir528 mutant and the miR5280E line and undiseased lines obtained in step I are used as experimental materials to detect the relative enzyme activity of OsAO of each material. The specific experimental steps refer to step I of example 1.

Figure 12:
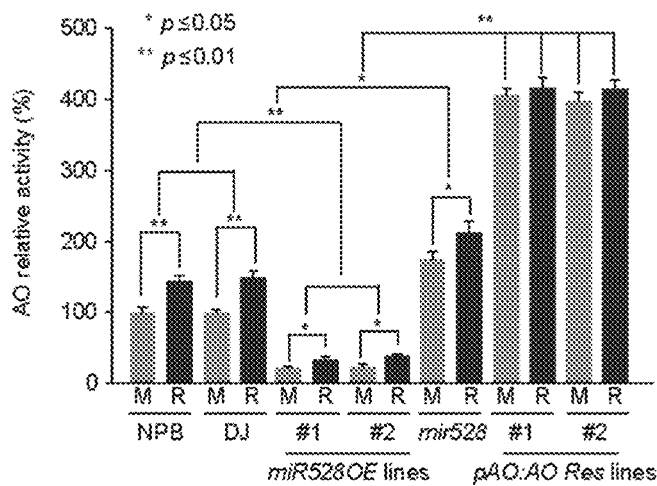
FIG. 12 is detection result of relative enzyme activity of OsAO in mock-(M) or RBSDV-inoculated(R) DJ, NPB, mir528, and pAO:AO-Res or miR5280E transgenic lines in example 3. In the uninfected rice, the enzyme activity of OsAO in pAO:AO-Res and miR5280E lines increased significantly relative to WT, while declined sharply in miR5280E line. And the enzyme activity of OsAO shows dramatic rise after RSV infection.

The results are shown in FIG. 12. The enzyme activity of OsAO is significantly enhanced after RBSDV infection, indicating that OsAO has function during the infection of RBSDV.

Based on the above experimental results, it is shown that OsAO plays a role in plant anti-RBSDV process and can enhance the resistance of plants to rice black-streaked dwarf virus.

The invention claimed is:

1. A method of improving plant resistance to rice stripe disease and rice black-streaked dwarf disease, comprising expressing a protein according to an amino acid sequence of SEQ ID NO: 4 in the plant, wherein expressing the protein in the plant comprises the following steps:

a) importing a gene encoding the protein according to SEQ ID NO: 4 into the plant, and obtaining a transgenic plant;

b) selecting transgenic plants with enhanced resistance to rice stripe disease, rice black-streak dwarf disease.

2. The method of claim 1, wherein the gene is any one of SEQ ID NO: 1 or SEQ ID NO: 2.

3. The method of claim 1, wherein the plant is rice.

4. The method of claim 1, wherein the plant expressing the protein according to an amino acid sequence of SEQ ID NO: 4 is resistant to a pathogen of rice stripe disease selected from rice stripe virus(RSV), a pathogen of rice black-streaked dwarf disease selected from rice black-streaked dwarf virus(RBSDV), wherein a viral mediator of both viruses is *Laodelphax striatellus*.

* * * * *

SEQUENCE LISTING

<160> NUMBER OF SEQ ID NOS: 30

<210> SEQ ID NO 1
<211> LENGTH: 5472
<212> TYPE: DNA
<213> ORGANISM: Oryza sativa

<400> SEQUENCE: 1
atagtgtagc atagctcact tccaagagcc tcgtgacaca caccactcac tatactggcc 60
cctcctcctc ctcggagatc gagccggcca gccatggcgg ccgccgtgca gctgctcgtc 120
gtcgccgccg ccgccgccat ggcggcggcg tgctgcgccg gcatggcggc ggcggcggcg 180
acggtggagg tgacgtggga cgtggagtac gtactgtggg cgccggactg ccagcagcgg 240
gtgatgatcg ggataaacgg caggttcccg gggcccaaca tcaccgcgcg cgccggcgac 300
gtgatcagcg tcaccatgaa caacaagatg cacaccgagg gcgtcgtcat ccactggcac 360
ggcatcagac aggtactagt acactctact ggtagcatag tgaccggaca aagttttaca 420
atcatacagt tccttctttt tttttttca agtcgaaacc aacgttatac tttctccata 480
taaaaaaaat atatgagatt ttgggtggat gggacacatc ctagtgcaac gaatctgaac 540
cgtctatcca cccaaaatcc cttatatatt aagacggaga gagtatatag ttattcggtc 600
catactagaa tataataact tcttatgttt aatataataa cttcttgtgt ttaacttttt 660
attaaaatat aatattttat cttaaaatat aacaacttta tcgatataac ttgacaaatg 720
tatatacttc ctccgtttca aaatgtaagt cattctaact tttcccacat tcatattcat 780
gttaataaat ctagataaat atatatgtat tcgttaatat caatatgaat atgggaaatg 840
ttagaatgac ttacatgtga aacggatgga gtacatggat tctctttagt ctcagcgaat 900
cataagtatt tctctttttt tctctatcta ctttcacata tcaactaatc attatcatta 960
gtcatataat tttatttact ttattaatct agtgtcaccg cctcgaactg gccactggtt 1020
ttctagcaac ccctaaaaca ggaaaacacg aagaagattt tatttttgaa caggaaaagc 1080
tcaaagtaaa ttgtcgtgtg tttgaaaaga aaaggcacaa actaataaag cgggtctatc 1140
tggattctgg aaccacccac actgcaccac cgtcagtgtc gcttccgaag ttgcgagaaa 1200
caactttgct ttagaataac ttgttctctt tttaaaaaaa tacagtttgt gaaaaaaaaa 1260
tcgtagttta acttaacttt gtaacagagt ataagcccta ctctgctttt atattttcct 1320

-continued

```
tttatgcact aaccagctcg agcacagcct aaaacttaag aaaaaaaatt atgattctta   1380
agaggcatgg agaggtatta ataacttttg aagtatagtt ttttttatct tctcgtagta   1440
ttgagaagtg gcaaattttg tacttaactg tgtaaaaaat agtacctctc attttcttct   1500
caaagaacta taaatttact caaaacaaca taaactgagt agaaactaga aaggtcatgc   1560
attttactta ctataacagt aatctaaact actacacaac tacgagtttt ataattctag   1620
aatgaatata atgaaaaatg atgtaaaatc aattaccacg catgcagttt ggcacgccgt   1680
gggcggacgg gacggcatcg atatcccagt gcgcagtgaa cccgggcgag acgttcgtct   1740
acaagttcgt cgccgacaag ccgggcacct acttctacca cggccacttc gggatgcagc   1800
gcgccgcggg cctgtacggt tccctcatcg tcctcgactc gccggagcag cccgagccgt   1860
tccgccacca gtacgacgac ggcggcgagc tccccatgat gctcctcagc gactggtggc   1920
accagaacgt ctacgcccag gccgccggac tcgacggcaa ggacaggcac ttcgagtgga   1980
tcggcgagcc ccaggtaaat aaaaaaacac atcgccgccg tcgtcatcgt cgccgccatc   2040
tccggtgata gagaaccatg tcgataaaga aggcacgatg ggtcacccgt gccttcaggc   2100
cggcacggca cggctcgact cgcctcgggc cgtgcctagc ccgtgtcggg cggcccttat   2160
ggccatctat accggtgagt gctaacagtt agttttttgc aaattgtaga cgatcttgat   2220
caatgggaga ggacagttcg agtgcacgct ggggccagcg aggaagagct ttgagaagct   2280
cctcaacgag aacgtggaga cctgcgtcga cgaccagaag atgtgcagcg accaggagaa   2340
gtgcctgagg aggagcgagt gcgggccgta ctgccccagg agccagtgcg cccctgtcgt   2400
gttcaatgtc gagcagggga agacttaccg ccttaggatc gccagcacca cctccctttc   2460
tctcctcaac gtcaagattc aaggggtaag ataattcaat gttttttatg gattgtattt   2520
tttagattgt acgaaagacg cacgtatact atcatgatgt ataataaggg agcataaatg   2580
taagtatact gatttaatca cgctcgaaaa tatatgaatg agtgtcggtc atcatcttca   2640
acagtagctt gatgtgactt gttgtaacaa tttcaatgaa attgaagaaa ttttgcaaat   2700
ggtaaaattt tggcagcaca agatgacggt ggtggaggcc gacgggaacc acgtggagcc   2760
gttcgtggtc gacgacatcg acatctactc cggcgagagc tactccgtcc tcctcaaggc   2820
cgaccagaag ccggcgagct actggatctc cgtcggcgtc agggggcgcc accccaagac   2880
ggtgccggcg ctcgccatcc tcagctacgg caacggcaac gcggcgccgc cgccgctcca   2940
gctgcccgcc ggcgagcccc ccgtgacgcc ggcgtggaac gacacacagc gcagcaaggc   3000
cttcacctac agcatcaggg cgcgcaagga caccaaccgg ccgccgccgg cggccgccga   3060
ccggcagatc gtcctgctca acacgcagaa cctcatggac gggcgctaca ggtggtccat   3120
caacaacgtg tccctgacgc tgccggcgac gccgtacctg ggcgccttcc accacggcct   3180
ccaggacagc gcgttcgacg cgtccggcga gccgccggcg gcgttcccgg aggactacga   3240
cgtgatgagg ccgccggcga acaacgcgac gacggcgagc gacagggtgt tccggctgcg   3300
acacggcggc gtggtggacg tggtgctcca gaacgccaac atgctgaggg aggaggtgag   3360
cgagacgcac ccgtggcacc tccacggcca cgacttctgg gtgctcggct acggcgacgg   3420
ccggtacgac ccggcggcgc acgcggcggg gctcaacgcc gccgacccgc cgctgcggaa   3480
cacggcggtg gtcttcccgc acgggtggac ggcgcttcgg ttcgtcgcca acaacaccgg   3540
cgcgtgggcg ttccactgcc acatcgagcc gcacctccac atgggcatgg gcgtcgtctt   3600
cgtcgagggg gaggacagga tgcacgagct cgacgtgccc aaggacgcca tggcgtgcgg   3660
```

-continued

```
cctcgtcgcc aggacggccg ccacgccgct caccccggca acgccgctgc ctccgtcgcc   3720

ggcgccggcg ccatgagctc ctcctcagca tgcccattcc agttaaatgc catttttgcc   3780

gtaacattgt gattggccac tgcgaaataa gatcactcac tgatgaagag tggtttagat   3840

tgtttggtca tatgcatgct caataatctc atgtaactaa gaaataatgt ccatgtttgc   3900

taattaagat gattgtgtaa tattgttgca atgtacacca aaaatattgc acggtgttgc   3960

tggcaaagag tggacaccca gcacaagcaa atctccagct agtggatagc aaaccatgat   4020

aaagtacgta tgttcgaatg tgatatgcct caaatctcca gaaaaagaaa tatgtgaagc   4080

cgtaagataa agagacatgg aatattacaa gaagcactca aacatcttca gagttacaaa   4140

attcatgtca cgctacaggg agtatcaaga actctcttga acatcaggca attcttacct   4200

cctaccagac tacatgttct accaaaaacc atccaatccg gtcgcacatc ccacttccat   4260

ttatatatgt taattgggag acaccattgt atcacatttg tagcagatga tgtttcgagc   4320

tgtctcatca gtcgatcttc acagaagcat atatcttcct cacgaaccag aagcaagcat   4380

agaagccaat ggtaccagtc agcacgaaga aagcatacga gatgatcagc atgtaaccaa   4440

agtagagaat gcctgaaaca agcttcgtga tctccagctt gttgaagaag tagaagatgg   4500

cataagcaaa aagatacagt gctgaagagc cagcagtcag gtatgctctc caccaccagt   4560

gatagtcctc gctgcatagt tggaagtagc agagcacaat tgtgatctca gcacaagtaa   4620

cgatgaggat gatgaagact atgaagagga agccgaagat gtagtagaac tggttcagcc   4680

agattgatgt cagaatgaag aagagctcga tgaagacagc gccaaatggc aatatgccac   4740

cagcaagtat tgagaaagct ggctgcaggt accatgcctg ctcaggaatt tgcctgggaa   4800

tcttgtttgt cttcactggg tcctcaatgg ctggctgctt gaagcccaag aaacttccaa   4860

caaagactag cggcacagag atgccaaacc aaaggaggaa cagagcaaac attgttccaa   4920

agggaactgc acctgatgat ttctcacccc agatcagggc atttaggaag aaaaagagtg   4980

caaagattat accaggaaac ataaaggcag tcttgagggt gattttcttc cattcagtgc   5040

ctttgaacat cttatatagg cgagatgagg tgtatcctgc caatacaccc atgaacaccc   5100

acagaaggac catagcagtc attagtccac cacggtttgc aggggacaag aatccaagta   5160

gcgcaaacat catggttacc agtgtcattc caaagaactg cacaccagtt ccaacataaa   5220

cacaaaggag gcctgagtgg acaggtggcc tgaagacatc accatgcact aacttccagc   5280

cagtttcttc ctgggcctca tcctggttgt caagctgatt atagtttgca atatccttgt   5340

aaagagttct catcatgatc atggctacca tgccagaaag gaaaaggaca atcatcagtg   5400

agttaatgat tgagaaccaa tggatctggc tatcacttga aagaagatag acatcccaac   5460

gagatgccca ta                                                       5472
```

```
<210> SEQ ID NO 2
<211> LENGTH: 5472
<212> TYPE: DNA
<213> ORGANISM: Oryza sativa

<400> SEQUENCE: 2
```

```
atagtgtagc atagctcact tccaagagcc tcgtgacaca caccactcac tatactggcc     60

cctcctcctc ctcggagatc gagccggcca gccatggcgg ccgccgtgca gctgctcgtc    120

gtcgccgccg ccgccgccat ggcggcggcg tgctgcgccg gcatggcggc ggcggcggcg    180

acggtggagg tgacgtggga cgtggagtac gtactgtggg cgccggactg ccagcagcgg    240

gtgatgatcg ggataaacgg caggttcccg gggcccaaca tcaccgcgcg cgccggcgac    300
```

-continued

```
gtgatcagcg tcaccatgaa caacaagatg cacaccgagg gcgtcgtcat ccactggcac    360
ggcatcagac aggtactagt acactctact ggtagcatag tgaccggaca aagttttaca    420
atcatacagt tccttctttt tttttttca agtcgaaacc aacgttatac tttctccata    480
taaaaaaaat atatgagatt ttgggtggat gggacacatc ctagtgcaac gaatctgaac    540
cgtctatcca cccaaaatcc cttatatatt aagacggaga gagtatatag ttattcggtc    600
catactagaa tataataact tcttatgttt aatataataa cttcttgtgt ttaacttttt    660
attaaaatat aatattttat cttaaaatat aacaacttta tcgatataac ttgacaaatg    720
tatatacttc ctccgtttca aaatgtaagt cattctaact tttcccacat tcatattcat    780
gttaataaat ctagataaat atatatgtat tcgttaatat caatatgaat atgggaaatg    840
ttagaatgac ttacatgtga aacggatgga gtacatggat tctctttagt ctcagcgaat    900
cataagtatt tctctttttt tctctatcta ctttcacata tcaactaatc attatcatta    960
gtcatataat tttatttact ttattaatct agtgtcaccg cctcgaactg gccactggtt   1020
ttctagcaac ccctaaaaca ggaaaacacg aagaagattt tatttttgaa caggaaaagc   1080
tcaaagtaaa ttgtcgtgtg tttgaaaaga aaaggcacaa actaataaag cgggtctatc   1140
tggattctgg aaccacccac actgcaccac cgtcagtgtc gcttccgaag ttgcgagaaa   1200
caactttgct ttagaataac ttgttctctt tttaaaaaaa tacagtttgt gaaaaaaaaa   1260
tcgtagttta acttaacttt gtaacagagt ataagcccta ctctgctttt atattttcct   1320
tttatgcact aaccagctcg agcacagcct aaaacttaag aaaaaaaatt atgattctta   1380
agaggcatgg agaggtatta ataacttttg aagtatagtt ttttttatct tctcgtagta   1440
ttgagaagtg gcaaattttg tacttaactg tgtaaaaaat agtacctctc attttcttct   1500
caaagaacta taaatttact caaaacaaca taaactgagt agaaactaga aaggtcatgc   1560
attttactta ctataacagt aatctaaact actacacaac tacgagtttt ataattctag   1620
aatgaatata atgaaaaatg atgtaaaatc aattaccacg catgcagttt ggcacgccgt   1680
gggcggacgg gacggcatcg atatcccagt gcgcagtgaa cccgggcgag acgttcgtct   1740
acaagttcgt cgccgacaag ccgggcacct acttctacca cggccacttc gggatgcagc   1800
gcgccgcggg cctgtacggt tccctcatcg tcctcgactc gccggagcag cccgagccgt   1860
tccgccacca gtacgacgac ggcggcgagc tccccatgat gctcctcagc gactggtggc   1920
accagaacgt ctacgcccag gccgccggac tcgacggcaa ggacaggcac ttcgagtgga   1980
tcggcgagcc ccaggtaaat aaaaaaacac atcgccgccg tcgtcatcgt cgccgccatc   2040
tccggtgata gagaaccatg tcgataaaga aggcacgatg ggtcacccgt gccttcaggc   2100
cggcacggca cggctcgact cgcctcgggc cgtgcctagc ccgtgtcggg cggcccttat   2160
ggccatctat accggtgagt gctaacagtt agtttttttgc aaattgtaga cgatcttgat   2220
caatgggaga ggacagttcg agtgcacgct ggggccagcg aggaagagct ttgagaagct   2280
cctcaacgag aacgtggaga cctgcgtcga cgaccagaag atgtgcagcg accaggagaa   2340
gtgcctgagg aggagcgagt gcgggccgta ctgccccagg agccagtgcg cccctgtcgt   2400
gttcaatgtc gagcagggga agacttaccg ccttaggatc gccagcacca cctccctttc   2460
tctcctcaac gtcaagattc aaggggtaag ataattcaat gttttttatg gattgtattt   2520
tttagattgt acgaaagacg cacgtatact atcatgatgt ataataaggg agcataaatg   2580
taagtatact gatttaatca cgctcgaaaa tatatgaatg agtgtcggtc atcatcttca   2640
```

-continued

```
acagtagctt gatgtgactt gttgtaacaa tttcaatgaa attgaagaaa ttttgcaaat   2700
ggtaaaattt tggcagcaca agatgacggt ggtggaggcc gacgggaacc acgtggagcc   2760
gttcgtggtc gacgacatcg acatctactc cggcgagagc tactccgtcc tcctcaaggc   2820
cgaccagaag ccggcgagct actggatctc cgtcggcgtc agggggcgcc accccaagac   2880
ggtgccggcg ctcgccatcc tcagctacgg caacggcaac gcggcgccgc cgccgctcca   2940
gctgcccgcc ggcgagcccc ccgtgacgcc ggcgtggaac gacacacagc gcagcaaggc   3000
cttcacctac agcatcaggg cgcgcaagga caccaaccgg ccgccgccgg cggccgccga   3060
ccggcagatc gtcctgctca acacgcagaa cctcatggac gggcgctaca ggtggtccat   3120
caacaacgtg tccctgacgc tgccggcgac gccgtacctg ggcgccttcc accacggcct   3180
ccaggacagc gcgttcgacg cgtccggcga gccgccggcg gcgttcccgg aggactacga   3240
cgtgatgagg ccgccggcga acaacgcgac gacggcgagc gacagggtgt tccggctgcg   3300
acacggcggc gtggtggacg tggtgctcca gaacgccaac atgctgaggg aggaggtgag   3360
cgagacgcac ccgtggcacc tccacggcca cgacttctgg gtgctcggct acggcgacgg   3420
ccggtacgac ccggcggcgc acgcggcggg gctcaacgcc gccgacccgc cgctgcggaa   3480
cacggcggtg gtcttcccgc acgggtggac ggcgcttcgg ttcgtcgcca acaacaccgg   3540
cgcgtgggcg ttccactgcc acatcgagcc gcacctccac atgggcatgg gcgtcgtctt   3600
cgtcgagggg gaggacagga tgcacgagct cgacgtgccc aaggacgcca tggcgtgcgg   3660
cctcgtcgcc aggacggccg ccacgccgct caccccggca acgccgctgc ctccgtcgcc   3720
ggcgccggcg ccatgagctc cacgtcacga aactcatcca agttaaatgc catttttgcc   3780
gtaacattgt gattggccac tgcgaaataa gatcactcac tgatgaagag tggtttagat   3840
tgtttggtca tatgcatgct caataatctc atgtaactaa gaaataatgt ccatgtttgc   3900
taattaagat gattgtgtaa tattgttgca atgtacacca aaaatattgc acggtgttgc   3960
tggcaaagag tggacaccca gcacaagcaa atctccagct agtggatagc aaaccatgat   4020
aaagtacgta tgttcgaatg tgatatgcct caaatctcca gaaaaagaaa tatgtgaagc   4080
cgtaagataa agagacatgg aatattacaa gaagcactca aacatcttca gagttacaaa   4140
attcatgtca cgctacaggg agtatcaaga actctcttga acatcaggca attcttacct   4200
cctaccagac tacatgttct accaaaaacc atccaatccg gtcgcacatc ccacttccat   4260
ttatatatgt taattgggag acaccattgt atcacatttg tagcagatga tgtttcgagc   4320
tgtctcatca gtcgatcttc acagaagcat atatcttcct cacgaaccag aagcaagcat   4380
agaagccaat ggtaccagtc agcacgaaga aagcatacga gatgatcagc atgtaaccaa   4440
agtagagaat gcctgaaaca agcttcgtga tctccagctt gttgaagaag tagaagatgg   4500
cataagcaaa aagatacagt gctgaagagc cagcagtcag gtatgctctc caccaccagt   4560
gatagtcctc gctgcatagt tggaagtagc agagcacaat tgtgatctca gcacaagtaa   4620
cgatgaggat gatgaagact atgaagagga agccgaagat gtagtagaac tggttcagcc   4680
agattgatgt cagaatgaag aagagctcga tgaagacagc gccaaatggc aatatgccac   4740
cagcaagtat tgagaaagct ggctgcaggt accatgcctg ctcaggaatt tgcctgggaa   4800
tcttgtttgt cttcactggg tcctcaatgg ctggctgctt gaagcccaag aaacttccaa   4860
caaagactag cggcacagag atgccaaacc aaaggaggaa cagagcaaac attgttccaa   4920
agggaactgc acctgatgat ttctcacccc agatcagggc atttaggaag aaaaagagtg   4980
caaagattat accaggaaac ataaaggcag tcttgagggt gattttcttc cattcagtgc   5040
```

```
ctttgaacat cttatatagg cgagatgagg tgtatcctgc caatacaccc atgaacaccc   5100

acagaaggac catagcagtc attagtccac cacggtttgc aggggacaag aatccaagta   5160

gcgcaaacat catggttacc agtgtcattc caaagaactg cacaccagtt ccaacataaa   5220

cacaaaggag gcctgagtgg acaggtggcc tgaagacatc accatgcact aacttccagc   5280

cagtttcttc ctgggcctca tcctggttgt caagctgatt atagtttgca atatccttgt   5340

aaagagttct catcatgatc atggctacca tgccagaaag gaaaaggaca atcatcagtg   5400

agttaatgat tgagaaccaa tggatctggc tatcacttga aagaagatag acatcccaac   5460

gagatgccca ta                                                       5472


<210> SEQ ID NO 3
<211> LENGTH: 21
<212> TYPE: RNA
<213> ORGANISM: Oryza sativa

<400> SEQUENCE: 3

gaggagacgu acggggaagg u                                               21


<210> SEQ ID NO 4
<211> LENGTH: 633
<212> TYPE: PRT
<213> ORGANISM: Oryza sativa

<400> SEQUENCE: 4

Met Ala Ala Ala Val Gln Leu Leu Val Val Ala Ala Ala Ala Ala Met
1               5                   10                  15

Ala Ala Ala Cys Cys Ala Gly Met Ala Ala Ala Ala Ala Thr Val Glu
            20                  25                  30

Val Thr Trp Asp Val Glu Tyr Val Leu Trp Ala Pro Asp Cys Gln Gln
        35                  40                  45

Arg Val Met Ile Gly Ile Asn Gly Arg Phe Pro Gly Pro Asn Ile Thr
    50                  55                  60

Ala Arg Ala Gly Asp Val Ile Ser Val Thr Met Asn Asn Lys Met His
65                  70                  75                  80

Thr Glu Gly Val Val Ile His Trp His Gly Ile Arg Gln Phe Gly Thr
                85                  90                  95

Pro Trp Ala Asp Gly Thr Ala Ser Ile Ser Gln Cys Ala Val Asn Pro
            100                 105                 110

Gly Glu Thr Phe Val Tyr Lys Phe Val Ala Asp Lys Pro Gly Thr Tyr
        115                 120                 125

Phe Tyr His Gly His Phe Gly Met Gln Arg Ala Ala Gly Leu Tyr Gly
    130                 135                 140

Ser Leu Ile Val Leu Asp Ser Pro Glu Gln Pro Glu Pro Phe Arg His
145                 150                 155                 160

Gln Tyr Asp Asp Gly Gly Glu Leu Pro Met Met Leu Leu Ser Asp Trp
                165                 170                 175

Trp His Gln Asn Val Tyr Ala Gln Ala Ala Gly Leu Asp Gly Lys Asp
            180                 185                 190

Arg His Phe Glu Trp Ile Gly Glu Pro Gln Thr Ile Leu Ile Asn Gly
        195                 200                 205

Arg Gly Gln Phe Glu Cys Thr Leu Gly Pro Ala Arg Lys Ser Phe Glu
    210                 215                 220

Lys Leu Leu Asn Glu Asn Val Glu Thr Cys Val Asp Asp Gln Lys Met
225                 230                 235                 240
```

```
Cys Ser Asp Gln Glu Lys Cys Leu Arg Arg Ser Glu Cys Gly Pro Tyr
                245                 250                 255

Cys Pro Arg Ser Gln Cys Ala Pro Val Val Phe Asn Val Glu Gln Gly
            260                 265                 270

Lys Thr Tyr Arg Leu Arg Ile Ala Ser Thr Thr Ser Leu Ser Leu Leu
        275                 280                 285

Asn Val Lys Ile Gln Gly His Lys Met Thr Val Val Glu Ala Asp Gly
    290                 295                 300

Asn His Val Glu Pro Phe Val Val Asp Asp Ile Asp Ile Tyr Ser Gly
305                 310                 315                 320

Glu Ser Tyr Ser Val Leu Leu Lys Ala Asp Gln Lys Pro Ala Ser Tyr
                325                 330                 335

Trp Ile Ser Val Gly Val Arg Gly Arg His Pro Lys Thr Val Pro Ala
            340                 345                 350

Leu Ala Ile Leu Ser Tyr Gly Asn Gly Asn Ala Ala Pro Pro Pro Leu
        355                 360                 365

Gln Leu Pro Ala Gly Glu Pro Pro Val Thr Pro Ala Trp Asn Asp Thr
    370                 375                 380

Gln Arg Ser Lys Ala Phe Thr Tyr Ser Ile Arg Ala Arg Lys Asp Thr
385                 390                 395                 400

Asn Arg Pro Pro Pro Ala Ala Ala Asp Arg Gln Ile Val Leu Leu Asn
                405                 410                 415

Thr Gln Asn Leu Met Asp Gly Arg Tyr Arg Trp Ser Ile Asn Asn Val
            420                 425                 430

Ser Leu Thr Leu Pro Ala Thr Pro Tyr Leu Gly Ala Phe His His Gly
        435                 440                 445

Leu Gln Asp Ser Ala Phe Asp Ala Ser Gly Glu Pro Pro Ala Ala Phe
    450                 455                 460

Pro Glu Asp Tyr Asp Val Met Arg Pro Pro Ala Asn Asn Ala Thr Thr
465                 470                 475                 480

Ala Ser Asp Arg Val Phe Arg Leu Arg His Gly Gly Val Val Asp Val
                485                 490                 495

Val Leu Gln Asn Ala Asn Met Leu Arg Glu Glu Val Ser Glu Thr His
            500                 505                 510

Pro Trp His Leu His Gly His Asp Phe Trp Val Leu Gly Tyr Gly Asp
        515                 520                 525

Gly Arg Tyr Asp Pro Ala Ala His Ala Ala Gly Leu Asn Ala Ala Asp
    530                 535                 540

Pro Pro Leu Arg Asn Thr Ala Val Val Phe Pro His Gly Trp Thr Ala
545                 550                 555                 560

Leu Arg Phe Val Ala Asn Asn Thr Gly Ala Trp Ala Phe His Cys His
                565                 570                 575

Ile Glu Pro His Leu His Met Gly Met Gly Val Val Phe Val Glu Gly
            580                 585                 590

Glu Asp Arg Met His Glu Leu Asp Val Pro Lys Asp Ala Met Ala Cys
        595                 600                 605

Gly Leu Val Ala Arg Thr Ala Ala Thr Pro Leu Thr Pro Ala Thr Pro
    610                 615                 620

Leu Pro Pro Ser Pro Ala Pro Ala Pro
625                 630
```

<210> SEQ ID NO 5
<211> LENGTH: 15

<212> TYPE: PRT
<213> ORGANISM: Artificial Sequence
<220> FEATURE:
<223> OTHER INFORMATION: the sequence is synthesized
<220> FEATURE:
<221> NAME/KEY: PEPTIDE
<222> LOCATION: (1)..(15)

<400> SEQUENCE: 5

Asp Ser Pro Glu Gln Pro Glu Pro Phe Arg His Gln Tyr Asp Asp
1 5 10 15

<210> SEQ ID NO 6
<211> LENGTH: 4600
<212> TYPE: DNA
<213> ORGANISM: Oryza sativa

<400> SEQUENCE: 6
acataggatc ctaaaagagt tgtggcgatt tgggacctag atgacatacc cctacaagag 60
tctaaggacc gcccgtgcac tttataaaaa atatatatat agcttccaat atatcccaat 120
tcccaaaaca atcaagatga aaactaaaaa aaagaaaaga aaagaaaagg aaccagtgca 180
tgcatgcatg aatatgcagg ggtgagctgg tgtgcatgca tgtgtttccg agtgtgcgcc 240
acatgagtct cgcgcgcgag atagcaaacc cgtgttgagt ttatcttaat ttctttttgt 300
ttgatggatt ggttaaattt ggacttagtt tgagtgagat gcatgacata acatagatat 360
ataagtacat tgaatcagtg ctgaaccttt ctttttttccc tcctaagatt gtccacaact 420
gcttatatgg tttttgtgcg aggggggat cgacacgtca gtaccacatc gtctagcgct 480
gcacaggtac agtagcagct agcgctacct tacaacgtcg gatcgcagca agatccggca 540
cgcgctgtct cgctacagcg aaatggctgc agcgctcgat gtaagtatag ctaactactg 600
gctctaattc atctataacc aatctaatag cttatttata taatagtaca tactatacta 660
ttaatacctg gttccacatg tcatacacac cttgcgtctt gaagtccgtg ctatagctgg 720
ctataaattt gtagcccgct gctcttctct ctccttattt atcttcttaa aatatatttg 780
cagctggctt attgtacctg ctctaaacgc tacgtacaca gtacgtgcca cgcgtacggc 840
cggtagggcc ctatatgttc ccgacgccta ctaccgaaca cagttgataa gatgagttta 900
tggatatgaa atagatagaa tgaagaagag agaaacgtct atatgttaat taagcttaat 960
attggttttt aagtgtttac aaaaggaaat ttgttataat atgagaatgc gtaaagtaaa 1020
agaaagctaa tttataattc ttttggtgca ttaatttttc gagtgtttgt aaacctgttg 1080
ttgtaagaga atatatattg aacgaactaa acgtccaaac aaggctttac tttcaggatt 1140
agactaaaat agctactttc ctttaggctt gttaatttaa tttagtcttt tatatttttt 1200
atctctttct taaatggcta cttcgttaga aaggttgcaa ggttattgat ggaaactaga 1260
aaaagttgtc tattgggttg gtaatgatcg actttaggcc tgggttgtct agctacatgc 1320
aacccgtgac tagaatcccg ggtgtatttt cacagacgtg tcttcaaata aataaaggga 1380
tgtcatcaaa ataatttttg tagtgcaata aattatgtca ttggaaaagg attaagaata 1440
tatcatgtca gtattacgga ttaggtatat cttctatact tgaattccta accgccatac 1500
cacataccta atataaagta tgcttataag agaatataat agataagaaa gaaaactctt 1560
tccacggaaa taaaaggtat cggacttcga ccaaggaaag caatgtctta tatatatccg 1620
tattctataa aagctccccg agttttactt ggacaagaag ttgcatatat ccatataaat 1680
acaaaactcc ttaggaggaa gtcgatcata agttagccac gagccacatt gagaatcact 1740

```
cacgaggaaa tcgatcgcta gccaccaact ccaagtcatt agattagtta gcttaactta   1800
aggctgtgtt cttttgaagg ggttgggaac ccctcccctc cgcacgaaaa acggagtgat   1860
agattaacat gtgattaatt aagtattagc tataaaaaat taaaaaatag attaatatga   1920
cttttaaaaa caaatttctt atataaactt tttataaaac gtgtaccatt tagcgggttt   1980
aaaaagcgtg cacgcgaaaa acgagggagg tgggttggga acccatggag aagaacacag   2040
cctattatac ctatctgaga tgtcaaacca gtataaaatt ccttatcttc cgtctatttt   2100
gttgtaatct cgcgtatacc ctggcatcaa tgtttcttat actatacaaa taccgttatc   2160
gggtatagca ctttgatata ttgaaagatg ggataataag tcacgtactc ctctgggaaa   2220
tgaccagctt aaaagctaac aaaattcaca ttagttagtg agtacctttt ctggaccgtg   2280
gttataagct tctttagcaa tagctaccat atatgtgtgt cgtcagtgtg tgcttgtaac   2340
tttgcaagtt gtaacaaatg gctagttagc tcatatatgg tacatcttta ggtggatatg   2400
taagataata ttcctacaat tgtaacaatt tgctactccc tttgtttcaa aataaaataa   2460
tttttagcat tcaaaatttg tcttaaaata taacaactta tatacctata ttttcttctc   2520
aaccaatcac aacctttcac cattcaaatt attcaattat ttctcttctc aatcaatcat   2580
aacctcctcc gattgaattt caactgattt cttaatatcc gtgtctaatc ctaaaacttc   2640
ttatatttag aacgaatgta tggtattatg gtactactat ctatggcctc gtttagttgg   2700
ggaaaatttt tgggtttggt tgtcacatca gatataccga cacacattta aagtattaaa   2760
cgtagtctaa taacagaaca aattatagat tccgccagaa aaatgcgaga cgaatttatt   2820
aagcctaaat aatccattat tagcaaaagt ttaatgtagc accacattgt caaatcatgg   2880
cacaattagg cttaaaagat tcgtctcgca atttacacgc aatctgtgta attggttttt   2940
tttcttacat ttaatactcc atgcatgtgt acaaacattc gatgtggcag cgtgtttttg   3000
ttctgggaac taaacagagc ctatatatgc agatttacta ctggagaagt gatttttgct   3060
aggtcggctg atagactaaa aattgttttt aagtcccggt taaaattttt ttgatcttta   3120
gtcccggttg gtgttaccaa ccgagtaaag attatttaga tctttaatcc cggttggtat   3180
tatcaaacgg gagtaaaaat ccatctttaa atatttctct cccatctccg atcgattaag   3240
tcccagacga gactttcctc ctcaccgaga tatttaaata agatcggatc ataccctctc   3300
ctcctacccc ttagatcccc ttcctcctcc cctcccctct cttcctcccc ttcctcctcc   3360
cctcccctct tctcccoctc ctcccctccc atccggcgga caacggcgac aagctggcgg   3420
ccagcgggcg gtggggccac gcacggcggt gcccggcggg gccacgcatg gggctgcagg   3480
cggcaggcgg cagccgtggc gagtggcggc aggcggcggc cgtggcaggc ggcggcagct   3540
ggcgggaggg gaggcgcgca tgcataggcc gggcgccctc tcctctaccg gtgtcccttt   3600
tttttatata atttgtgatt cattgatatg tataatttct tttttttag aatttgtgat   3660
tcattacatg gatctgatat gtataatctg tgatgtattt gatttgtgtg tattttttta   3720
ggatttgtga tgtatttgat ttgtgtgtat aagtaactta ggatttgtga tgtgaataat   3780
ttgggatgtt actttgattt gaggatatgc gtggcactcg atttgggaga aaatataagg   3840
attaactcta gcaagtagca aagaaacaat aaaaaaaaaa agaaaagggg accaaccgga   3900
actgtcacta ctctctcttt agtcccggtt ggtgtaaaga ttcaacttta ctcctggtta   3960
tttcacccgg gattaaagat gggtatcttt agtcccggat ttatagcctc ggttaaaaaa   4020
ccgagactac agggggtccc aaccggaatt acaaacggtt tctccggtag tgattgttca   4080
tcaatgattg ctgacacata attgacaact ttggaattat attaggggca tgctgccccc   4140
```

atggacgaac gagcaagact aagacgttat cggtcagtaa tgtccacaca cgaggtatat 4200
caagtgaaaa ccatcgaata aataaaaact catcaaaatt agatttaaag ttctcaatct 4260
tctaaagaaa attcctagag atacgtatag gcatgaaatc ttgagcccaa ttaaccttca 4320
tttgaagaaa aaaggtatta ttcatcttaa aacagtttgg ctttgaccaa agttaaaatg 4380
tcttataacc taaaacggag ggagtattac acagcaacca agtactacaa acaagcagaa 4440
aatttcgtgc tcaaggaatc tcccatatca gcatgtttcc aaacataaca gaaatttaat 4500
ttacacccta cttaatttta ttacccctca caaaacatga ataaccaatg cagctaatct 4560
gggcacacct atatataaag aaagaaagca tggcctcccc 4600

<210> SEQ ID NO 7
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 7
cgagaacgtg gagacctgcg tcga 24

<210> SEQ ID NO 8
<211> LENGTH: 25
<212> TYPE: DNA
<213> ORGANISM: Artificial Sequence
<220> FEATURE:
<223> OTHER INFORMATION: the sequence is synthesized

<400> SEQUENCE: 8
ccaccaccgt catcttgtgc ccttg 25

<210> SEQ ID NO 9
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 9
gcacgctctt cttgctttca ctct 24

<210> SEQ ID NO 10
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 10
aaaggtcacc accataccag gctt 24

<210> SEQ ID NO 11
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 11
cgagaacgtg gagacctgcg tcga 24

<210> SEQ ID NO 12

<211> LENGTH: 25
<212> TYPE: DNA
<213> ORGANISM: Artificial Sequence
<220> FEATURE:
<223> OTHER INFORMATION: the sequence is synthesized

<400> SEQUENCE: 12
ccaccaccgt catcttgtgc ccttg 25

<210> SEQ ID NO 13
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 13
gcacgctctt cttgctttca ctct 24

<210> SEQ ID NO 14
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 14
aaaggtcacc accataccag gctt 24

<210> SEQ ID NO 15
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 15
gcacccaata ggtatctcct tgat 24

<210> SEQ ID NO 16
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 16
caaatgaccc tactagatgg acga 24

<210> SEQ ID NO 17
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 17
caaccaccct tatcacaaac ttca 24

<210> SEQ ID NO 18
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 18
caccaatacc tttccctgac accc 24

<210> SEQ ID NO 19
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 19
tatatgggca ccaacaagcc agcc 24

<210> SEQ ID NO 20
<211> LENGTH: 27
<212> TYPE: DNA
<213> ORGANISM: Artificial Sequence
<220> FEATURE:
<223> OTHER INFORMATION: the sequence is synthesized

<400> SEQUENCE: 20
tatgacttag ggagtgagtt gtgcagt 27

<210> SEQ ID NO 21
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 21
gcttcaccac accgaactcc ttct 24

<210> SEQ ID NO 22
<211> LENGTH: 24
<212> TYPE: DNA
<213> ORGANISM: Artificial Sequence
<220> FEATURE:
<223> OTHER INFORMATION: the sequence is synthesized

<400> SEQUENCE: 22
gttacgattg accaagctgc caca 24

<210> SEQ ID NO 23
<211> LENGTH: 19
<212> TYPE: DNA
<213> ORGANISM: Artificial Sequence
<220> FEATURE:
<223> OTHER INFORMATION: the sequence is synthesized

<400> SEQUENCE: 23
aacccagtca agacgctca 19

<210> SEQ ID NO 24
<211> LENGTH: 20
<212> TYPE: DNA
<213> ORGANISM: Artificial Sequence
<220> FEATURE:
<223> OTHER INFORMATION: the sequence is synthesized

<400> SEQUENCE: 24
cgacatcaaa tgaagcacct 20

<210> SEQ ID NO 25
<211> LENGTH: 20
<212> TYPE: DNA

-continued

```
<213> ORGANISM: Artificial Sequence
<220> FEATURE:
<223> OTHER INFORMATION: the sequence is synthesized

<400> SEQUENCE: 25

tgtgataaca gaatgacggc                                          20


<210> SEQ ID NO 26
<211> LENGTH: 19
<212> TYPE: DNA
<213> ORGANISM: Artificial Sequence
<220> FEATURE:
<223> OTHER INFORMATION: the sequence is synthesized

<400> SEQUENCE: 26

cttcggtcgg acaatacac                                           19


<210> SEQ ID NO 27
<211> LENGTH: 19
<212> TYPE: DNA
<213> ORGANISM: Artificial Sequence
<220> FEATURE:
<223> OTHER INFORMATION: the sequence is synthesized

<400> SEQUENCE: 27

tcagcagtct tgggttgat                                           19


<210> SEQ ID NO 28
<211> LENGTH: 20
<212> TYPE: DNA
<213> ORGANISM: Artificial Sequence
<220> FEATURE:
<223> OTHER INFORMATION: the sequence is synthesized

<400> SEQUENCE: 28

cagtttcagc agagtaacgc                                          20


<210> SEQ ID NO 29
<211> LENGTH: 18
<212> TYPE: DNA
<213> ORGANISM: Artificial Sequence
<220> FEATURE:
<223> OTHER INFORMATION: the sequence is synthesized

<400> SEQUENCE: 29

attggcgaag tgttgagc                                            18


<210> SEQ ID NO 30
<211> LENGTH: 19
<212> TYPE: DNA
<213> ORGANISM: Artificial Sequence
<220> FEATURE:
<223> OTHER INFORMATION: the sequence is synthesized

<400> SEQUENCE: 30

cgggtgctaa atgaaatgc                                           19
```